US007547696B2

(12) United States Patent
Aranyi et al.

(10) Patent No.: US 7,547,696 B2
(45) Date of Patent: Jun. 16, 2009

(54) AMINOQUINOLINE DERIVATIVES AND THEIR USE AS ADENOSINE A3 LIGANDS

(75) Inventors: Peter Aranyi, Budapest (HU); Sandor Batori, Budapest (HU); Geza Timari, Vecses (HU); Kinga Boer, Budapest (HU); Zoltan Kapui, Budapest (HU); Endre Mikus, Budapest (HU); Katalin Urban-Szabo, Budapest (HU); Katalin Gerber, Budapest (HU); Judit Vargane Szeredi, Budapest (HU); Michel Finet, Budapest (HU)

(73) Assignee: sanofi-aventis, Paris (FR)

( * ) Notice: Subject to any disclaimer, the term of this patent is extended or adjusted under 35 U.S.C. 154(b) by 1 day.

(21) Appl. No.: 11/344,440

(22) Filed: Jan. 31, 2006

(65) Prior Publication Data

US 2006/0211689 A1 Sep. 21, 2006

Related U.S. Application Data

(63) Continuation of application No. PCT/HU2004/000080, filed on Jul. 23, 2004.

(30) Foreign Application Priority Data

| | | |
|---|---|---|
| Jul. 31, 2003 | (HU) | 0302440 |
| Jul. 21, 2004 | (HU) | 0401467 |
| Jul. 21, 2004 | (HU) | 0401468 |

(51) Int. Cl.
*A61K 31/535* (2006.01)
*C07D 413/12* (2006.01)

(52) U.S. Cl. .................................... 514/235.2; 544/128

(58) Field of Classification Search ................. 544/128; 514/235.2

See application file for complete search history.

(56) References Cited

U.S. PATENT DOCUMENTS 6,969,723 B2 11/2005 Aranyi et al.

FOREIGN PATENT DOCUMENTS

| | | |
|---|---|---|
| EP | 0566226 | 10/1993 |
| EP | 1180514 | 2/2002 |
| WO | WO98/43960 | 10/1998 |
| WO | WO 02/096879 | 12/2002 |

OTHER PUBLICATIONS

Science (1999), vol. 286, 531-537.*

Rimmer et al., Clinical and Experimental Allergy, 37, 8-14 (2007).*

Kreckler et al., The Journal of Pharmacology and Experimental Therapeutics, vol. 317, No. 1, pp. 172-180 (2006).*

Gessi et al., Pharmacology & Therapeutics 117(2008) 123-140.*

Nakamura et al., Anticancer Res. 2006; 26(1A);43-47, abstract only.*

Burduliene, et al., Chloroethyl derivatives of 2,5-diaminobenzoic acid, Database Beilstein, Beilstein Institute for Organic Chemistry, XP002299337, vol. 4, (1973) pp. 55-58.

Carboni, S., Researches in the field of pyridine. I. 2-Amino-5-nitronicotinic acid, Database Beilstein, Beilstein Institute for Organic Chemistry, XP002299336, Abstract vol. 83, (1953), pp. 637-640.

Hynes, J.B., et al., Improved Synthesis and Antitumor Evaluation of 5,8-Dideazaisofolic Acid and Closely Related Analogues, J. Med. Chem. 1984, 27, 232-235.

Jakobsen, et al., Inhibitors of the Tissue Factor/Factor VIIa-Induced Coagulation: Synthesis and In Vitro Evaluation of Novel Specific 2-Aryl Substituted 4H-3,1-Benzoxazin-4-ones, Bioorganic & Medicinal Chemistry 8 (2000) 2095-2103.

Chou et al., Beilstein Abstract No. 9271163.

Chou et al., Structure-Activity Relationships of Substituted Benzothiopheneanthranilamide Factor Xa Inhibitors, Bioorg. Med. Chem. Lett. 13(2003), pp. 507-511.

* cited by examiner

*Primary Examiner*—Rebecca L Anderson
(74) *Attorney, Agent, or Firm*—Brian R. Morrill

(57) ABSTRACT

The present invention relates to an adenosine $A_3$ receptor ligand of the general formula (I), within those preferably to the antagonists, including a salt, solvate or isomer (tautomer, desmotrop, and optically active isomer) thereof, to a pharmaceutical composition containing the ligand, to the use of the ligand, to its preparation, and intermediates of the ligand of the general formula (II"), (III"), (IV"), (V"), (VI"), (VII"), (VIII") and (XIII") and their preparation.

8 Claims, No Drawings

AMINOQUINOLINE DERIVATIVES AND THEIR USE AS ADENOSINE A3 LIGANDS

CROSS REFERENCE

This application is a continuation of PCT Application HU2004/000080, filed 23 Jul. 2004, which designated the United States.

FIELD OF THE INVENTION

The present invention relates to an adenosine $A_3$ receptor ligand of the general formula (I), within those preferably to the antagonists, including a salt, solvate or isomer (tautomer, desmotrop, and optically active isomer) thereof, to a pharmaceutical composition containing the ligand, to the use of the ligand, to its preparation, and intermediates of the ligand of the general formula (II"), (III"), (IV"), (V"), (VI"), (VII"), (VIII") and (XIII") and their preparation.

BACKGROUND OF THE INVENTION

Adenosine is a well-known component of several endogenous molecules (ATP, $NAD^+$, nucleic acids). It plays an important regulatory role in many physiological processes. The effect of adenosine on the heart function was described already in 1929 (Drury and Szentgyörgyi, Physiol. 68:213, 1929). The identification of an increasing number of physiological functions mediated by adenosine and the discovery of new adenosine receptor subtypes are offering possibilities for the therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for the inhibition of the adenylate cyclase by coupling to $G_i$ membrane protein, and partly influences other second messenger systems. The $A_2$ receptor subtype can be subdivided into two further subtypes—$A_{2a}$ and $A_{2b}$—which stimulate the adenylate cyclase activity. The sequence of the adenosine $A_3$ receptors have been first identified from rat testis cDNA library. Later it was proved that it corresponds to a novel, functional adenosine receptor. The activation of the $A_3$ receptors is also connected with several second-messenger systems: inhibiting of adenylate cyclase, stimulating phospholipase C and D.

The adenosine receptors are found in several organs and regulate their functions. Both $A_1$ and $A_{2a}$ receptors play important role in the central nervous system and cardiovascular system. In the CNS, the adenosine inhibits the release of synaptic transmitters which effect is mediated by $A_1$ receptors. In the heart, the $A_1$ receptors also mediate the negative inotropic, chronotropic and dromotropic effects of adenosine. The adenosine $A_{2a}$ receptors, which are located in a relatively high amount in the striatum, display functional interaction with the dopamine receptors in regulating the synaptic transmission. The $A_{2a}$ adenosine receptors on endothelial and smooth muscle cells are responsible for adenosine-induced vasodilation.

On the basis of RNA identification, the $A_{2b}$ adenosine receptors are widely distributed in different tissues. They have been identified in almost every cell type, but its expression is the highest in the intestine and the bladder. This subtype probably also has important regulatory function in the regulation of the vascular tone and plays a role in the function of mast cells.

Contrary to $A_1$ and $A_{2a}$ receptors, where the tissue distribution was detected on the protein level, the presence of $A_{2b}$ and $A_3$ receptors was detected on the basis of their mRNA level. Expression levels for $A_3$ adenosine receptors are rather low compared to other subtypes and they are highly species dependent. $A_3$ adenosine receptors are expressed primarily in the central nervous system, in the testis and in the immune system, and appear to be involved in the modulation of the mediator release from the mast cells in immediate hypersensitivity reaction.

For therapeutic use, it is essential to ensure that the molecule does not bind, or binds only in the case of very high concentration to the $A_1$, $A_{2a}$ and $A_{2b}$ sub-types of the adenosine receptor.

$A_3$ antagonists published so far in the literature, belong to the groups of flavonoides, 1,4-dihydropyridine derivatives, triazoloquinazolines, thiazolonaphthyridines and thiazolopyrimidines. Most of the effective and for the adenosine subtypes selective antagonists, however posses strong lipophilic character, and they are therefore sparingly soluble in water. This feature hinders the in vivo applicability of the compounds. In the literature more and more studies are to find aiming the preparation of water-soluble adenosine A3 receptor antagonists (Ch. E. Müller et al., J. Med. Chem. 45:3440, 2002; A. Maconi et al., J. Med. Chem. 45:3579, 2002).

Patent application WO 02/096879 discloses 2-amino-3-cyanoquinoline derivatives as structurally novel type, effective $A_3$ antagonists. The compounds described in patent application WO 02/096879 are $A_3$ antagonists with high selectivity of the following general formula:

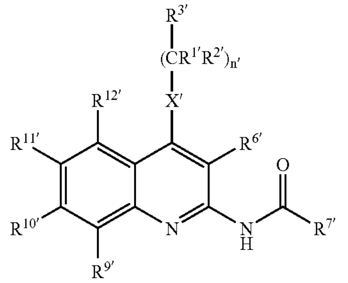

$R^{1'}$ stands for hydrogen atom or straight or branched $C_{1-4}$ alkyl group;

$R^{2'}$ stands for hydrogen atom or straight or branched $C_{1-4}$ alkyl group;

$R^{3'}$ stands for hydrogen atom or straight or branched $C_{1-4}$ alkyl group, phenyl, thienyl, or furyl group, optionally substituted with one or more straight or branched $C_{1-4}$ alkyl group, straight or branched $C_{1-4}$ alkoxy group or halogen atom; a six- or five-membered heteroaromatic ring containing one, two or three nitrogen atoms, or one nitrogen atom and one oxygen atom, or one nitrogen atom and one sulphur atom, optionally substituted with one or more straight or branched $C_{1-4}$ alkyl group, straight or branched $C_{1-4}$ alkoxy group or halogen atom;

$R^{9'}$, $R^{10'}$, $R^{11'}$, and $R^{12'}$ independently stand for hydrogen atom, straight or branched $C_{1-4}$ alkyl group, straight or branched $C_{1-4}$ alkoxy group, hydroxy group or halogen atom, or $R^{9'}$ and $R^{12'}$ stand for hydrogen atom and $R^{10'}$ and $R^{11'}$ form together a methylenedioxy group;

$R^{6'}$ stands for hydrogen atom or a cyano group, aminocarbonyl group, $C_{1-4}$ alkoxycarbonyl group, or carboxy group;

$R^{7'}$ stands for hydrogen atom or straight or branched $C_{1-4}$ alkyl group, phenyl, benzyl, thienyl, or furyl group, optionally substituted with methylenedioxy-group or with one or more straight or branched $C_{1-4}$ alkyl group, straight or branched $C_{1-4}$ alkoxy group, hydroxy group, trifluoromethyl group, cyano group or halogen atom; or a six- or five-membered heteroaromatic ring containing one, two or three nitrogen atoms, or one nitrogen atom and one oxygen atom, or one nitrogen atom and one sulphur atom, optionally substituted with one or more straight or branched $C_{1-4}$ alkyl group, straight or branched $C_{1-4}$ alkoxy group or halogen atom;

X' stands for —$CH_2$— group, —NH— group, —$NR^{8'}$— group, or sulphur atom, oxygen atom, sulpho group or sulphoxy group, wherein $R^{8'}$ stands for straight or branched $C_{1-4}$ alkyl group or $C_{3-6}$ cycloalkyl group;

n' represents zero, 1 or 2;

These compounds too, have the characteristic disadvantage that they are only sparingly soluble, which hampers their development into a drug. What would be useful would be compounds having solubility profiles that are far better than those of the known 2-amino-3-cyanoquinolines, besides, and which would also be highly active.

SUMMARY OF THE INVENTION

The instant invention is directed to a compound of the general formula (I), (I)

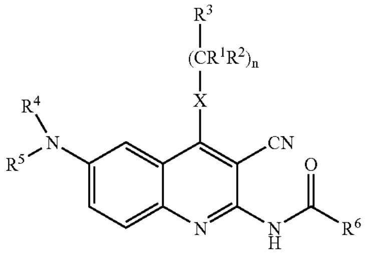

wherein $R^1$ stands for hydrogen atom or a straight or branched $C_{1-4}$ alkyl;

$R^2$ stands for hydrogen atom or a straight or branched $C_{1-4}$ alkyl;

$R^3$ stands for hydrogen atom, straight or branched $C_{1-4}$ alkyl, or $C_{3-6}$ cycloalkyl, phenyl, thienyl, or furyl which is optionally substituted with one or more straight or branched $C_{1-4}$ alkyl, straight or branched $C_{1-4}$ alkoxy, or halogen atom, or six- or five-membered heteroaromatic ring containing one, two or three nitrogen atoms, or five-membered heteroaromatic ring containing one nitrogen atom and one oxygen atom, or one nitrogen atom and one sulphur atom, which heteroaromatic ring is optionally substituted with one or more straight or branched $C_{1-4}$ alkyl, straight or branched $C_{1-4}$ alkoxy, or halogen atom;

$R^4$ and $R^5$ independently stand for hydrogen atom, $C_{3-6}$ cycloalkyl, straight or branched $C_{1-4}$ alkyl which is optionally substituted by a hydroxy, carboxy, or straight or branched $C_{1-4}$ alkoxy, amino or amino substituted with one or two straight or branched $C_{1-4}$ alkyl; or $R^4$ stands for hydrogen atom, straight or branched $C_{1-4}$ alkyl or benzyl, and $R^5$ stands for hydrogen atom, —$SO_2OH$ or straight or branched $C_{1-4}$ acyl, or $R^4$ and $R^5$ taken together with the nitrogen atom to which they are attached form a group of the general formula a.)

a.)

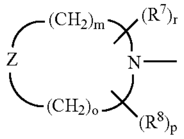

$R^6$ stands for hydrogen atom or straight or branched $C_{1-4}$ alkyl, phenyl, benzyl, thienyl, or furyl, each of which is optionally substituted with methylenedioxy, or one or more straight or branched $C_{1-4}$ alkyl, straight or branched $C_{1-4}$ alkoxy, hydroxy, trifluoromethyl, cyano or halogen atom, or six- or five-membered heteroaromatic ring containing one, two or three nitrogen atoms, or one nitrogen atom and one oxygen atom, or one nitrogen atom and one sulphur atom, which heteroaromatic ring is optionally substituted with one or more straight or branched $C_{1-4}$ alkyl, straight or branched $C_{1-4}$ alkoxy or halogen atom;

$R^7$ and $R^8$ independently stand for hydrogen atom, straight or branched $C_{1-4}$ alkyl or $C_{3-6}$ cycloalkyl;

X stands for —$CH_2$—, —NH—, —$NR^9$—, or sulphur atom, oxygen atom, sulpho or sulphoxy;

$R^9$ stands for straight or branched $C_{1-4}$ alkyl or $C_{3-6}$ cycloalkyl;

Z stands for oxygen atom, sulphur atom, —$CHR^{10}$— or —$NR^{11}$—;

$R^{10}$ stands for hydrogen atom, straight or branched $C_{1-4}$ alkyl, or $C_{3-6}$ cycloalkyl;

$R^{11}$ stands for hydrogen atom, straight or branched $C_{1-4}$ alkyl, $C_{3-6}$ cycloalkyl, —$SO_2OH$ or straight or branched $C_{1-4}$ acyl;

n represents zero, 1 or 2;

m represents 1, 2, or 3;

o represents 1, 2, or 3;

p represents zero or 1; and r represents zero or 1, or a salt, solvate, or isomer (tautomer, desmotrop, optically active isomer) thereof, or a salt or solvate of the isomer. The compound of the general formula (I) have a high selectivity for the $A_3$ sub-type of the adenosine receptor.

DETAILED DESCRIPTION OF THE INVENTION

Our aim was to prepare $A_3$ ligands, within them preferably antagonists, with quinoline structure, which exert strong antagonistic effect and high selectivity for the $A_3$ receptor, i.e. they inhibit the $A_3$ receptor in much lower concentration than they inhibit the $A_1$, $A_{2a}$ and $A_{2b}$ receptors. Further aims were to have stability, bioavailability, therapeutic index, toxicity and solubility data, which enable these new compounds to develop into drug substances, and that the new compounds possess favourable enteric absorption to be applied orally.

As shown by liquid phase NMR studies, in solution the compound of the general formula (I) is in equilibrium mixtures of the tautomeric forms (IA) and (IB):

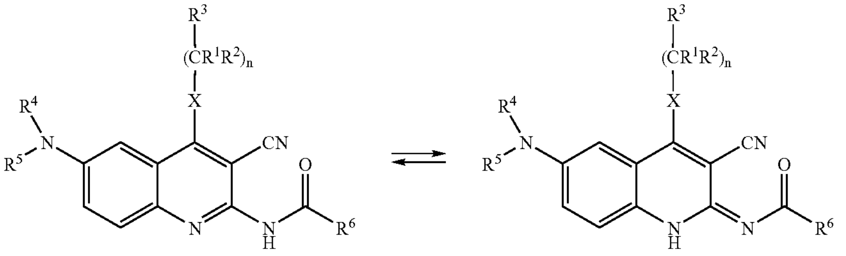

(IA) (IB)

In solid phase the tautomers (IA) and (IB) can be isolated separately, as the desmotrop (IA) or (IB).

According to the above findings, the present invention also relates to the desmotropic isomers (IA) and (IB). The meanings of the substituents in the general formulae (IA) and (IB) are as defined for the general formula (I).

The compound of the general formula (I) may have a chiral centre depending for instance on the meaning of the set of substituents $R^1$, $R^2$, and $R^3$. Thus, the invention also relates to the racemic form or an optically active form of the compound of the general formula (I), or a salt, tautomer or desmotrop thereof.

Definition of Terms

Detailed meanings of the above substituents are as follows:

By a straight or branched $C_{1-4}$ alkyl we mean a methyl, ethyl, propyl, isopropyl, butyl, isobutyl, secondary-butyl or tertiary-butyl, preferably ethyl or methyl.

By a straight or branched $C_{1-4}$ alkoxy we mean a methoxy, ethoxy, propoxy, isopropoxy, butoxy, isobutoxy, secondary-butoxy, tertiary-butoxy, preferably ethoxy or methoxy.

By a $C_{3-6}$ cycloalkyl we mean a cyclopropyl, cyclobutyl, cyclopentyl or cyclohexyl.

By a straight or branched $C_{1-4}$ acyl we mean a formyl, acetyl, propionyl, 2-methyl-propionyl, or butyryl.

By the heteroaromatic ring containing one, two or three nitrogen atoms we mean a pyrrole, imidazole, pyrazole, 1,2,3-triazole, 1,2,4-triazole, pyridine, pyrimidine, pyridazine, pyrazine or 1,2,4-triazine ring. The ring may optionally be substituted with a $C_{1-4}$ alkyl, $C_{1-4}$ alkoxy, or halogen atom.

By the heteroaromatic ring containing one nitrogen atom and one oxygen- or one sulphur atom we mean an oxazole, isoxazole, thiazole or isothiazole ring. The ring may optionally be substituted with a $C_{1-4}$ alkyl, $C_{1-4}$ alkoxy, or halogen atom.

The a.) group a.)

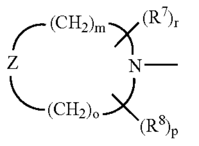

preferably represents a pyrrolidino, piperidino, piperazino, 4-methylpiperazino, 4-formylpiperazino, 4-sulfonylpiperazino or morpholino.

By a salt of the compound of the general formula (I) we mean a salt formed with inorganic or organic acids and bases. Preferred salts are given with pharmaceutically accepted acids, as for instance hydrochloric acid, sulphuric acid, ethanesulphonic acid, tartaric acid, malic acid, citric acid, fumaric acid, and with pharmaceutically accepted bases, as for instance NaOH, potassium hydroxide, and ethanolamine. Salts used for purification or isolation, as for instance the methanesulphonate or tetrafluoroborate salts are also subjects of the invention.

By a solvate we mean a solvate of various solvents, as for instance of water or ethanol.

By an isomer we mean a tautomer, desmotrop, or optically active isomer.

Particular or Preferred Embodiments of the Invention

A favoured embodiment of the compound of the general formula (I) is wherein $R^1$ stands for hydrogen atom or a straight or branched $C_{1-4}$ alkyl;

$R^2$ stands for hydrogen atom or a straight or branched $C_{1-4}$ alkyl;

$R^3$ stands for hydrogen atom, a straight or branched $C_{1-4}$ alkyl or $C_{3-6}$ cycloalkyl, a phenyl, thienyl, or furyl, each of which is optionally substituted with one or more straight or branched $C_{1-4}$ alkyl, straight or branched $C_{1-4}$ alkoxy, or halogen atom;

$R^4$ and $R^5$ independently stand for hydrogen atom, $C_{3-6}$ cycloalkyl, straight or branched $C_{1-4}$ alkyl which is optionally substituted by a hydroxy, carboxy, straight or branched $C_{1-4}$ alkoxy, amino, or amino substituted with one or two straight or branched $C_{1-4}$ alkyl; or $R^4$ stands for hydrogen atom or a straight or branched $C_{1-4}$ alkyl or a benzyl, and $R^5$ stands for hydrogen atom, —$SO_2OH$ or a straight or branched $C_{1-4}$ acyl, or $R^4$ and $R^5$ taken together with the nitrogen atom to which they are attached form a group of the general formula a.)

a.)

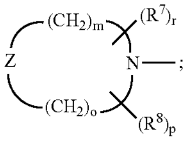

$R^6$ stands for hydrogen atom or straight or branched $C_{1-4}$ alkyl, phenyl, benzyl, thienyl, or furyl, each of which is optionally substituted with methylenedioxy, or with one or more straight or branched $C_{1-4}$ alkyl, straight or branched $C_{1-4}$ alkoxy, hydroxy, trifluoromethyl, cyano, or halogen atom; or six- or five-membered heteroaromatic ring containing one, two or three nitrogen atoms, or one nitrogen atom and one oxygen atom, or one nitrogen atom and one sulphur atom, which heteroaromatic ring is optionally substituted with one or more straight or branched $C_{1-4}$ alkyl, straight or branched $C_{1-4}$ alkoxy or halogen atom;

$R^7$ and $R^8$ independently stand for hydrogen atom, straight or branched $C_{1-4}$ alkyl or $C_{3-6}$ cycloalkyl;

X stands for —$CH_2$—, —NH—, —$NR^9$—, or sulphur atom, oxygen atom, sulpho or sulphoxy;

$R^9$ represents a straight or branched $C_{1-4}$ alkyl or $C_{3-6}$ cycloalkyl;

Z stands for oxygen atom, sulphur atom, —$CHR^{10}$— or —$NR^{11}$—;

$R^{10}$ represents hydrogen atom, straight or branched $C_{1-4}$ alkyl, or $C_{3-6}$ cycloalkyl;

$R^{11}$ stands for hydrogen atom, straight or branched $C_{1-4}$ alkyl, $C_{3-6}$ cycloalkyl, —$SO_2OH$ or formyl;

n represents zero, 1 or 2;

m represents 1, 2, or 3;

o represents 1, 2, or 3;

p represents zero or 1; and r represents zero or 1, or a salt, solvate, or isomer (tautomer, desmotrop, optically active isomer) thereof, or a salt or solvate of the isomer.

A special embodiment of the compound of the general formula (I) is wherein $R^1$ stands for hydrogen atom or methyl;

$R^2$ stands for hydrogen atom or methyl;

$R^3$ stands for phenyl, thienyl, or furyl;

$R^4$ and $R^5$ independently stand for hydrogen atom, $C_{3-6}$ cycloalkyl, straight or branched $C_{1-4}$ alkyl which is optionally substituted by a hydroxy, carboxy, or straight or branched $C_{1-4}$ alkoxy, amino, or amino substituted with one or two straight or branched $C_{1-4}$ alkyl, or $R^4$ stands for hydrogen atom or a straight or branched $C_{1-4}$ alkyl or a benzyl, and $R^5$ stands for hydrogen atom, —$SO_2OH$ or a straight or branched $C_{1-4}$ acyl, or $R^4$ and $R^5$ taken together with the nitrogen atom to which they are attached form a group of the general formula a.),

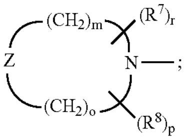

a.)

$R^6$ stands for 4-methoxyphenyl, 3-methylphenyl, 3-methoxyphenyl, 3,4-methylene-dioxyphenyl, 4-fluorophenyl, 2-thienyl or 2-furyl;

$R^7$ and $R^8$ independently stand for hydrogen atom, straight or branched $C_{1-4}$ alkyl or $C_{3-6}$ cycloalkyl;

X stands for —NH—, or oxygen atom;

Z stands for oxygen atom, sulphur atom, —$CH_2$—, —NH— or —$NR^{11}$—

$R^{11}$ represents a straight or branched $C_{1-4}$ alkyl, $C_{3-6}$ cycloalkyl, —$SO_2OH$ or formyl; and n represents 1;

m represents 2;

o represents 2;

p represents zero; and r represents zero, or a salt, solvate, or isomer (tautomer, desmotrop, optically active isomer) thereof, or a salt or solvate of the isomer.

Especially favoured is a compound selected from the following:

4-Methoxy-N-[6-(morpholin-4-yl)-4-benzylamino-3-cyano-quinolin-2-yl]-benzamide,

4-Methoxy-N-[6-(4-methylpiperazin-1-yl)-4-benzylamino-3-cyanoquinolin-2-yl]benzamide, 4-Methoxy-N-(6-dimethylamino-4-benzylamino-3-cyano-quinolin-2-yl)benzamide, 3,4-Methylenedioxy-N-(6-dimethylamino-4-benzylamino-3-cyanoquinolin-2-yl)benzamide, 4-Fluoro-N-(6-dimethylamino-4-benzylamino-3-cyano-quinolin-2-yl)benzamide, 4-Methoxy-N-(6-(piperazin-1-yl)-4-benzylamino-3-cyano-quinolin-2-yl)benzamide, 4-Methoxy-N-(6-amino-4-benzylamino-3-cyanoquinolin-2-yl)benzamide, N-[4-(Benzylamino)-3-cyano-6-(4-formylpiperazin-1-yl) quinolin-2-yl]-4-methoxybenzamide, 4-{4-(Benzylamino)-3-cyano-2-[(4-methoxybenzoyl) amino]quinolin-6-yl}piperazine-1-sulfonic acid, N-{3-Cyano-6-(formylamino)-4-[(2-thienylmethyl)amino] quinolin-2-yl}-4-methoxybenzamide, N-{3-Cyano-6-(formylamino)-4-[(2-thienylmethyl)amino] quinolin-2-yl}-1,3-benzodioxole-5-carboxamide, N-[4-(Benzylamino)-3-cyano-6-(formylamino)quinolin-2-yl]-1,3-benzodioxole-5-carboxamide, N-[4-(Benzylamino)-3-cyano-6-(formylamino)quinolin-2-yl]-4-methoxybenzamide, N-{4-(Benzylamino)-3-cyano-6-[formyl(methyl)amino] quinolin-2-yl}-4-methoxybenzamide, N-{3-Cyano-6-[formyl(methyl)amino]-4-[(2-thienylmethyl) amino]quinolin-2-yl}-4-methoxybenzamide, {3-Cyano-2-[(4-methoxybenzoyl)amino]-4-[(2-thienylmethyl)amino]quinolin-6-yl}methylsulfamic acid, {4-(Benzylamino)-3-cyano-2-[(4-methoxybenzoyl)amino] quinolin-6-yl}methylsulfamic acid, {4-(Benzylamino)-3-cyano-2-[(4-methoxybenzoyl)amino] quinolin-6-yl}sulfamic acid,

[2-[(1,3-Benzodioxol-5-ylcarbonyl)amino]-4-(benzylamino)-3-cyanoquinolin-6-yl]sulfamic acid, {2-[(1,3-Benzodioxol-5-ylcarbonyl)amino]-3-cyano-4-[(2-thienylmethyl)amino]quinolin-6-yl}sulfamic acid, and {3-Cyano-2-[(4-methoxybenzoyl)amino]-4-[(2-thienylmethyl)amino]quinolin-6-yl}sulfamic acid, or a salt, solvate, or isomer (tautomer, desmotrop, optically active isomer) thereof, or a salt or solvate of the isomer.

The compound of the general formula (I) according to the present invention as well as a salt, solvate, or isomer (tautomer, desmotrop, optically active isomer) thereof, or a salt or solvate of the isomer, displays suitable solubility, therefore can favourably be used as an active substance in a pharmaceutical composition.

Solubility values in water and in aqueous buffer solutions (pH=6.5 and 7.5) for the compound of the formula (1) of patent application WO 02/096879 are less than 1 mg/L, whereas those for the compound of the general formula (I) of the present invention are between 1-200 mg/L. The present invention also relates to a pharmaceutical composition containing as an active principle the compound of the general formula (I) or a salt, solvate, or isomer (tautomer, desmotrop, optically active isomer) thereof, or a salt or solvate of the isomer, which is preferably an oral composition, but an inhalable, parenteral and transdermal formulation is also an aspect of the invention. The above pharmaceutical compositions may be solids or liquids, such as tablets, pellets, capsules, patches, solutions, suspensions or emulsions. Solid compositions, first of all tablets and capsules are preferred.

The above pharmaceutical compositions are prepared by applying usual pharmaceutical auxiliary materials and by using standard methods.

The compound of the general formula (I) can be used for the treatment of pathologies, where $A_3$ receptor plays a role in the development of the disease.

The compound of the present invention having selective activity on the $A_3$ receptor can be used in the therapeutic and/or preventive treatment of disfunctions of the heart, kidney, respiratory system, central nervous system. It inhibits the protective effect of adenosine in growing tumor cells, prevent mast cell degranulation, inhibits the cytokine production, reduce the inraocular pressure, inhibits the TNFα release, inhibits the migration of eosinophils, neutrophils and other immune cells, and inhibits the bronchoconstriction and plasma extravasation.

Based on these effects, adenosine $A_3$ receptor antagonists of the present invention may be therapeutically useful as antiinflammatory, antiasthmatic, antiischemic, antidepressant, antiarrhytmic, renal protective, antitumor, antiparkinson and cognitive enhancing drugs. They also may be useful in the treatment or prevention of miocardial reperfusion injury, chronic obstructive pulmonary disease (COPD) and adult respiratory distress syndrome (ARDS) including chronic bronchitis, pulmonary emphysema or dyspnea, allergic reactions (e.g. rhinitis, poison ivy induced responses, urticaria, scleroderma, arthritis) other autoimmune diseases, inflammatory bowel disease, Addison's disease, Crohn's disease, psoriasis, rheumatism, hypertension, neurogical function disorders, glaucoma and diabetes (K. N. Klotz, Naunyn-Schmiedberg's Arch. Pharmacol. 362:382, 2000; P. G. Baraldi és P. A. Borea, TiPS 21:456, 2000).

The compound of the present invention may be preferably used for the manufacture of a pharmaceutical composition for the treatment of diseases such as asthma, COPD and ARDS, glaucoma, tumor, allergic and inflammatory diseases, ischemia, hypoxia, arrythmia and renal diseases.

The present invention relates furthermore to the use of the compound of the general formula (I) in the treatment of the above pathologies. The suggested daily dose is 0.1-1000 mg active ingredient, depending on the nature and severeness of the disease and on the sex, weight etc. of the patient.

A further aspect of the invention is the preparation of the compound of the general formula (I).

The substituents in the formulae of the intermediates and reagents of the general formulae (I"), (II"), (III"), (IV"), (V"), (VI"), (VII"), (VIII"), (IX"), (X"), (XI"), (XII"), (XIII") and (XIV"):

(I″)

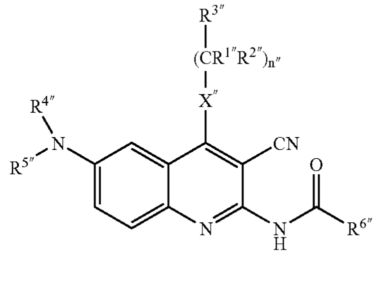

-continued (II″)

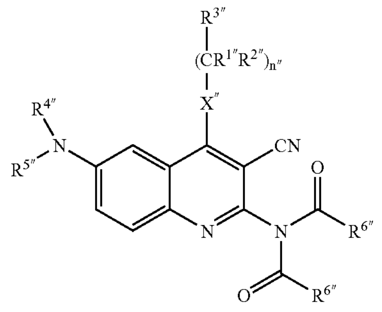

(III″)

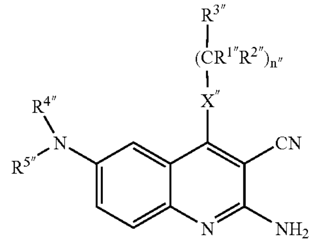

(IV″)

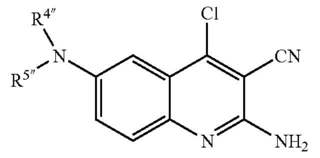

(V″)

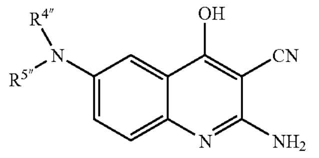

(VI″)

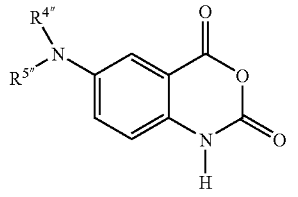

(VII″)

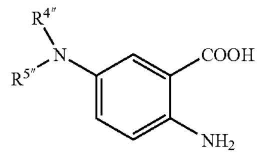

(VIII″)

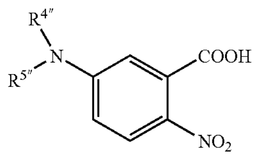

(IX″)

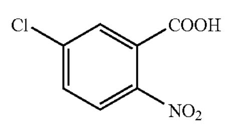

-continued (X")

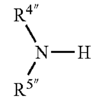

(XI")

$HX''—(CR^1R^2)_n—R^{3''}$ (XII")

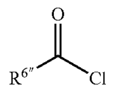

(XIII")

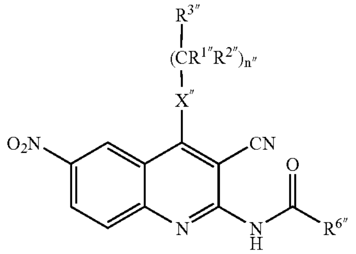

(XIV")

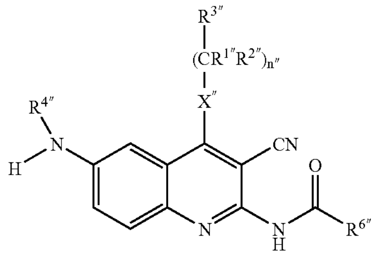

have the meanings as follows.

$R^{1''}$ stands for hydrogen atom or a straight or branched $C_{1-4}$ alkyl;

$R^{2''}$ stands for hydrogen atom or a straight or branched $C_{1-4}$ alkyl;

$R^{3''}$ stands for hydrogen atom, straight or branched $C_{1-4}$ alkyl, or $C_{3-6}$ cycloalkyl, phenyl, thienyl, or furyl, each of which is optionally substituted with one or more straight or branched $C_{1-4}$ alkyl, straight or branched $C_{1-4}$ alkoxy, or halogen atom; six- or five-membered heteroaromatic ring containing one, two or three nitrogen atoms, or five-membered heteroaromatic ring containing one nitrogen atom and one oxygen atom, or one nitrogen atom and one sulphur atom, which heteroaromatic ring is optionally substituted with one or more straight or branched $C_{1-4}$ alkyl, straight or branched $C_{1-4}$ alkoxy, or halogen atom;

$R^{4''}$ and $R^{5''}$ independently stand for hydrogen atom, $C_{3-6}$ cycloalkyl, straight or branched $C_{1-4}$ alkyl which is optionally substituted by a hydroxy, a carboxy, or straight or branched $C_{1-4}$ alkoxy, amino, amino substituted with one or two straight or branched $C_{1-4}$ alkyl, or protective group;

$R^{4''}$ stands for hydrogen atom or a straight or branched $C_{1-4}$ alkyl or a benzyl, and $R^{5''}$ stands for hydrogen atom, —$SO_2OH$, straight or branched $C_{1-4}$ acyl or protective group, or $R^{4''}$ and $R^{5'}$ taken together with the nitrogen atom to which they are attached form a group of the general formula a".)

a".)

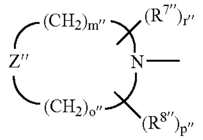

$R^{6''}$ stands for hydrogen atom or straight or branched $C_{1-4}$ alkyl, phenyl, benzyl, thienyl, or furyl, each of which is optionally substituted with methylenedioxy, or one or more straight or branched $C_{1-4}$ alkyl, straight or branched $C_{1-4}$ alkoxy, hydroxy, trifluoromethyl, cyano or halogen atom; or six- or five-membered heteroaromatic ring containing one, two or three nitrogen atoms, or one nitrogen atom and one oxygen atom, or one nitrogen atom and one sulphur atom, which heteroaromatic ring is optionally substituted with one or more straight or branched $C_{1-4}$ alkyl, straight or branched $C_{1-4}$ alkoxy or halogen atom;

$R^{7''}$ and $R^{8''}$ independently stand for hydrogen atom, straight or branched $C_{1-4}$ alkyl or $C_{3-6}$ cycloalkyl;

X" stands for —$CH_2$—, —NH—, —$NR^{9''}$—, or sulphur atom, oxygen atom, sulpho or sulphoxy;

$R^{9''}$ stands for straight or branched $C_{1-4}$ alkyl or $C_{3-6}$ cycloalkyl;

Z" stands for oxygen atom sulphur atom, —$CHR^{10}$ "— or —$NR^{11}$ "—;

$R^{10''}$ stands for hydrogen atom, straight or branched $C_{1-4}$ alkyl, or $C_{3-6}$ cycloalkyl;

$R^{11''}$ stands for hydrogen atom, straight or branched $C_{1-4}$ alkyl, $C_{3-6}$ cycloalkyl, —$SO_2OH$, straight or branched $C_{1-4}$ acyl or protective group;

$R^{12''}$ stands for straight or branched $C_{1-3}$ alkyl;

Y" represents leaving group;

n" represents zero, 1 or 2;

m" represents 1, 2, or 3;

o" represents 1, 2, or 3;

p" represents zero or 1;

r" represents zero or 1.

A further aspect of the invention is the preparation of the compound of the general formula (I) and of the partly novel intermediates of the general formulae (I"), (II"), (III"), (IV"), (V"), (VI"), (VII"), (VIII"), and (XIII").

In the process aspects according to the invention v.) the bis-carboxamide of the general formula (II") is selectively hydrolysed and if desired the protective group removed, or v/i.) for the preparation of a compound of the general formula (I), wherein $R^4$ stands for hydrogen atom, straight or branched $C_{1-4}$ alkyl or benzyl and $R^5$ stands for straight or branched $C_{1-4}$ acyl, or $R^4$ and $R^5$ taken together with the nitrogen atom to which they are attached form a group of the general formula a.), wherein Z stands for a —$NR^{11}$, where $R^{11}$ stands for a straight or branched $C_{1-4}$ acyl and $R^1$, $R^2$, $R^3$, $R^6$, $R^7$, $R^8$, $R^9$, X, n, m, o, p and r are as defined above, a compound of the general formula (I), wherein $R^4$ stands for hydrogen atom, a straight or branched $C_{1-4}$ alkyl or benzyl and $R^5$ stands for hydrogen atom, or $R^4$ and $R^5$ together with the nitrogen atom form a group of the general formula a.), wherein Z stands for —NH and $R^1$, $R^2$, $R^3$, $R^6$, $R^7$, $R^8$, $R^9$, X, n, m, o, p and r are as defined above, is acylated with a compound of the general formula $R^{12''}COY''$, wherein $R^{12''}$ and Y" are as defined above, or v/ii.) for the preparation of a compound of the general formula (I), wherein $R^4$ stands for hydrogen atom, a straight or branched $C_{1-4}$ alkyl or benzyl and $R^5$ stands for —$SO_2OH$, or $R^4$ and $R^5$ taken together with the nitrogen atom to which they are attached form a group of the general formula a.), wherein Z stands for —$NR^{11}$—, where $R^{11}$ stands for —$SO_2OH$ and $R^1$, $R^2$, $R^3$, $R^6$, $R^7$, $R^8$, $R^9$, X, n, m, o, p and r are as defined above, a compound of the general formula (I), wherein $R^4$ stands for hydrogen atom, a straight or branched $C_{1-4}$ alkyl or benzyl and $R^5$ stands for hydrogen atom, or $R^4$ and $R^5$ together with the nitrogen atom form a group of the general formula a.), wherein Z stands for —NH— and $R^1$, $R^2$, $R^3$, $R^6$, $R^7$, $R^8$, $R^9$, X, n, m, o, p and r are as defined above, is reacted with a pyridine-$SO_3$ complex, or with $ClSO_3H$, or v/iii.) for the preparation of a compound of the general formula (I), wherein $R^4$ stands for hydrogen atom, a straight or branched $C_{1-4}$ alkyl or benzyl and $R^5$ stands for —$SO_2OH$ and $R^1$, $R^2$, $R^3$, $R^6$, $R^7$, $R^8$, $R^9$, X, Z, n, m, o, p and r are as defined above, a compound of the general formula (XIII"), wherein $R^1$, $R^2$, $R^3$, $R^6$, $R^9$, X, and n are as defined above is reacted with $Na_2S_2O_4$ or $NaHSO_3$, or is reduced and the compound of the general formula (XIV"), thus obtained, wherein $R^{4''}$ stands for hydrogen atom and $R^{1''}$, $R^{2''}$, $R^{3''}$, $R^{6''}$, $R^{9''}$, X", and n", are as defined above, is sulphated with a pyridine-$SO_3$ complex or with $ClSO_3H$, if desired after transforming the $R^{4''}$ hydrogen atom into straight or branched $C_{1-4}$ alkyl or benzyl, or v/iv.) for the preparation of a compound of the general formula (I), wherein $R^4$ stands for hydrogen atom, $C_{3-6}$ cycloalkyl, benzyl, straight or branched $C_{1-4}$ alkyl which is optionally substituted by hydroxy, carboxy, or straight or branched $C_{1-4}$ alkoxy, amino, or amino substituted with one or two straight or branched $C_{1-4}$ alkyl, and $R^5$ stands for hydrogen atom, or $R^4$ and $R^5$, taken together with the nitrogen atom to which they are attached form a group of the general formula a.), wherein $R^7$ and $R^8$ independently stand for hydrogen atom, straight or branched $C_{1-4}$ alkyl or $C_{3-6}$ cycloalkyl and Z stands for —$NR^{11}$, where $R^{11}$ stands for hydrogen atom, removing the protective group of a compound of the general formula (I"), wherein $R^{4''}$ stands for hydrogen atom, $C_{3-6}$ cycloalkyl, benzyl, straight or branched $C_{1-4}$ alkyl which is optionally substituted by hydroxy, a carboxy, or straight or branched $C_{1-4}$ alkoxy, amino, or amino substituted with one or two straight or branched $C_{1-4}$ alkyl, and $R^{5''}$ stands for a protective group, or $R^{4''}$ and $R^{5''}$, taken together with the nitrogen atom to which they are attached form a group of the general formula a".), wherein $R^{7''}$ and $R^{8''}$ independently stand for hydrogen atom, straight or branched $C_{1-4}$ alkyl or $C_{3-6}$ cycloalkyl and Z stands for —$NR^{11''}$, where $R^{11''}$ stands for a protecting group, and—if desired—the substituents of the resulting compound of the general formula (I) are transformed into each other by known methods, and/or the compound of the general formula (I) thus obtained is transformed into its salt or solvate, or liberated from its salt or solvate and—if desired—resolved into its optically active isomers and—if desired—a given desmotrop is transformed into an other desmotropic form.

As for agents for the selective hydrolysis, alkali hydroxides, preferably potassium hydroxide and/or NaOH dissolved in an alcohol, preferably in methanol can be used, but other agents known in the organic chemistry helping the amide hydrolysis, can also be applied.

The selective hydrolysis can be carried out in a broad temperature range, preferable is the range between 20° C. and 100° C.

The reaction v/i.) can be performed using an ester derivative of the appropriate acid at elevated temperature or using an activated acid derivative (e.g. acid-halogenid) at room temperature or elevated temperature applying a suitable base (e.g. triethylamine).

The reaction v/ii.) can be performed using pyridine-$SO_3$ complex in a suitable solvent (preferably in pyridine) or using $ClSO_3H$ in a suitable solvent (preferably in pyridine or chloroform) applying a strong organic base (like DBU) or an inorganic base (like $K_2CO_3$) at room temperature or elevated temperature.

The reaction v/iii.) can be performed in an appropriate aqueous alkaline solution of the nitro compound using an excess of $Na_2S_2O_4$ or $NaHSO_3$ as reagent at room temperature or at elevated temperature (100°).

According to a variation of the reaction v/iii.) the nitro derivative is reduced by any of the known methods and the resulting amino derivative is alkylated or benzylated first under known reductive alkylation or benzylation conditions and the alkylamino or benzylamino derivatives, thus obtained will be sulphated as described under ii.).

The protective group may be any known protective group. Examples of protecting groups, as well as methods for protecting and deprotecting various functional groups are given in "Protective Groups in Organic Synthesis", Green et al., 2nd Edition *John Wiley & Sons, Inc, New York., 1991. Preferred protective groups are Boc, ethoxycarbonyl, benzyloxycarbonyl, etc, most preferably benzyl group.

The substituents of the compound of the general formula (I) can be transformed into each other by known methods (Comprehensive Organic Transformation, R. C. Larock, VCH Publisher, New York, 1989).

The salts can be prepared by adding one equivalent of the acid to the alcoholic, preferably ethanol solution of the base and diluting the solution with diethyl ether and finally filtering off and drying the resulting crystals.

The compound of the general formula (II")—wherein the meanings of $R^{1''}$, $R^{2''}$, $R^{3''}$, $R^{4''}$, $R^{5''}$, $R^{6''}$, $R^{7''}$, $R^{8''}$ X", Z", n", o", p", r" and m" are as defined above—can be prepared by several known methods, among them by the method demonstrated on reaction scheme 1., by acylation of the compound of formula (III") by an acylation method known from the organic chemistry. As for acylating agent preferably an acid chloride, for acid binding agent triethyl amine and/or pyridine can be used, but other compounds known as acid binders can also be applied.

The compound of the general formula (III")—wherein the meanings of $R^{1''}$, $R^{2''}$, $R^{3''}$, $R^{4''}$, $R^{5''}$, $R^{6''}$, $R^{7''}$, $R^{8''}$ X", Z", n", o", p", r" and m" are the same as defined above—can beprepared from the compound of formula (IV"), by methods known per se (Nan Zhang, Bioorg. and Med. Chem. Lett., 10, 2825, 2000).

The compound of the general formula (IV")—wherein the meanings of $R^{4''}$, $R^{5''}$, $R^{6''}$, $R^{7''}$, $R^{8''}$ X", Z", r", o", p" and m" are as defined above—can be prepared from the compound of formula (V"), by methods known per se (D. L. Leysen, J. Heterocyclic Chem., 24, 1611, 1987).

The compound of the general formula (V")—wherein the meanings of $R^{4''}$, $R^{5''}$, $R^{7''}$, $R^{8''}$, Z", r", o", p" and m" are as defined above—can be prepared from the compound of formula (VI"), by methods known per se (Pfizer (Inc) U.S. Pat. No. 4,175,193).

The compound of the general formula (VI")—wherein the meanings of $R^{4''}$, $R^{5''}$, $R^{7''}$, $R^{8''}$, Z", r", o", p" and m" are as defined above —can be prepared from the compound of formula (VII"), by methods known per se (D. L. Leysen, J. Heterocyclic Chem., 24, 1611, 1987).

The compound of the general formula (VII")—wherein the meanings of $R^{4''}$, $R^{5''}$, $R^{7''}$, $R^{8''}$, Z", r", o", p" and m" are as defined above —can be prepared from the compound of formula (VIII"), by methods known per se (D. H. Klaubert and J. H. Sellstedt, J. Med. Chem, 24, 742, 1981), or are products on the market, such as the compound where $R^{4''}$ and $R^{5''}$ together with the nitrogen atom form a nitro The compound of the general formula (VIII")—wherein the meanings of $R^{4''}$, $R^{5''}$, $R^{7''}$, $R^{8''}$, Z", r", o", p" and m" are as defined above —can be prepared from the compound of formula (IX"), by methods known per se (J. H. Hutchinson and J. J. Cook, J. Med. Chem. 39, 4583, 1996). The compound of the general formulae (I), (I') (II"), (III"), (IV"), (V"), (VI"), (VII"), (VIII"), (XIII") and (XIV") according to the invention, as well as their preparation and biological activity are demonstrated by the examples below, without limiting the claims to the examples.

Other aspects of the invention include the following intermediates:

Compounds of the general formula (I"), where in the formula the meanings of $R^{1''}$, $R^{2''}$, $R^{3''}$, $R^{6''}$, $R^{7''}$ $R^{8''}$ X", n", m", o", p", and r" are as defined in claim 5. and $R^{4''}$ stands for hydrogen atom, $C_{3-6}$ cycloalkyl, benzyl, straight or branched $C_{1-4}$ alkyl which is optionally substituted by hydroxy, carboxy, or straight or branched $C_{1-4}$ alkoxy, amino, or an amino substituted with one or two straight or branched $C_{1-4}$ alkyl, and $R^{5''}$ stands for a protective group, or $R^{4''}$ and $R^{5''}$, together with the nitrogen atom, form a group of the general formula a".), wherein $R^{7''}$ and $R^{8''}$ independently stand for hydrogen atom, straight or branched $C_{1-4}$ alkyl or $C_{3-6}$ cycloalkyl and Z stands for —$NR^{11''}$, where $R^{11''}$ stands for a protecting group.

Compounds of the general formula (II"), where in the formula the meanings of $R^{1''}$, $R^{2''}$, $R^{3''}$, $R^{4''}$, $R^{5''}$, $R^{6''}$, $R^{7''}$ $R^{8''}$ X", Z", n", m", o", p", and r" are as defined in claim 5.

Compounds of the general formula (III"), where in the formula the meanings of $R^{1''}$, $R^{2''}$, $R^{3''}$, $R^{4''}$, $R^{5''}$, $R^{7''}$, $R^{8''}$, X", Z", n", m", o", p", and r" are as defined in claim 5.

Compounds of the general formula (IV") where in the formula the meanings of $R^{4''}$, $R^{5''}$, $R^{7''}$, $R^{8''}$, Z", m", o", p", and r" are as defined in claim 5.

Compounds of the general formula (V"), where in the formula the meanings of $R^{4''}$, $R^{5''}$, $R^{7''}$, $R^{8''}$, Z", m", o", p", and r" are as defined in claim 5.

Compounds of the general formula (VI"), where in the formula the meanings of $R^{4''}$, $R^{5''}$, $R^{7''}$, $R^{8''}$, Z", m", o", p", and r" are as defined in claim 5., with the proviso that $R^{4''}$ and $R^{5''}$ together with the nitrogen atom, have a meaning different from dimethylamino- and amino.

Compounds of the general formula (VII"), where in the formulae the meanings of $R^{4''}$, $R^{5''}$, $R^{7''}$, $R^{8''}$, Z", m", o", p", and r" are as defined in claim 5., with the proviso that $R^{4''}$ and $R^{5''}$ together with the nitrogen, atom have a meaning different from dimethylamino-, diethylamino-, and amino.

Compounds of the general formula (VIII"), where in the formula $R^{4''}$ and $R^{5''}$ together with the nitrogen atom, represent a morpholino, N-methylpiperazino, piperazino or 4-benzylpyperazino.

Compounds of the general formula (XIII"), wherein the meanings of the substituents $R^{1''}$, $R^{2''}$, $R^{3''}$, $R^{6''}$ and n" are as defined in claim 5.

A scheme for preparing compounds according to the invention follows:

Reaction scheme 1

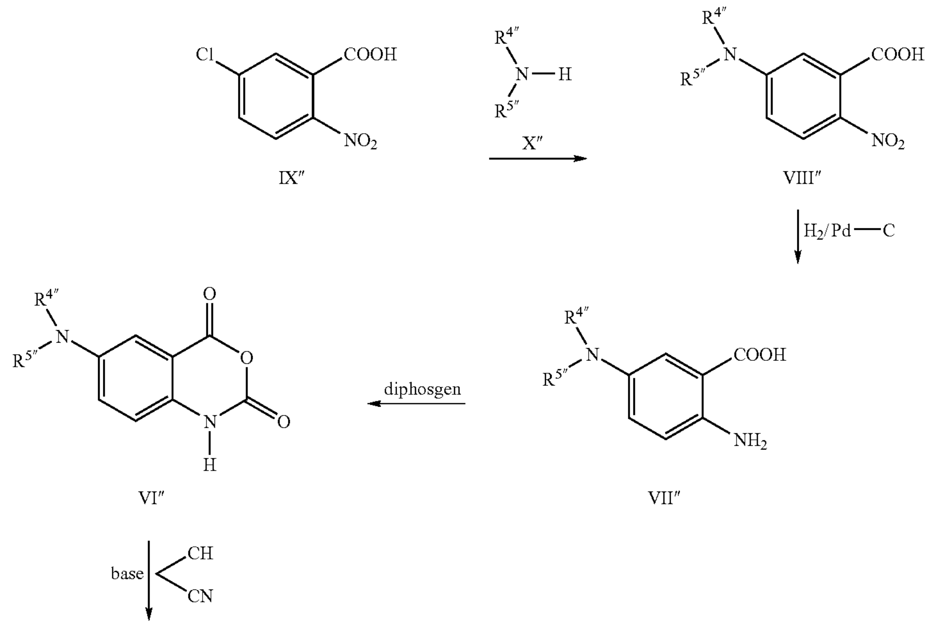

IX″ VIII″ VII″ VI″

-continued

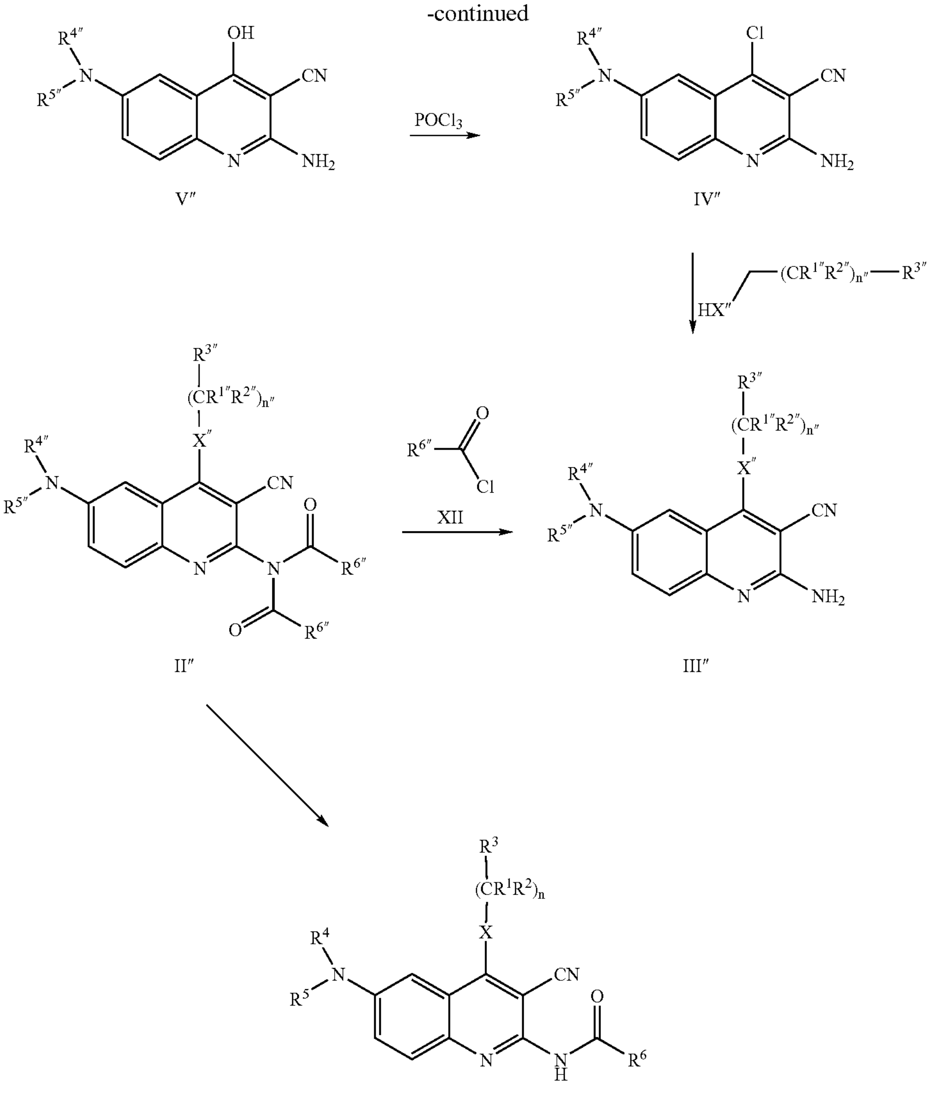

V″ IV″ II″ III″ I

EXAMPLES

Example 1

4-Methoxy-N-[6-(morpholin-4-yl)-4-benzylamino-3-cyanoquinolin-2-yl]benzamide In the general formula (I) $R^1$ and $R^2$ stand for hydrogen atom, $R^3$ for phenyl, group a.) for morpholino, $R^6$ for 4-methoxyphenyl, X for NH and the value of n is 1.

a.) 2-Nitro-5-(morpholin-4-yl)benzoic acid

The mixture of 5 g of 2-nitro-5-chlorobenzoic acid and 15 mL of morpholine is stirred at 120° C. for 6 hours. To the reaction mixture 150 mL of ethyl acetate is added. The precipitated yellow crystalline material is filtered off, dissolved in 15 mL of water. The pH of the mixture is adjusted to 6 with acetic acid. The precipitated material is filtered off, washed with water and dried, to obtain 4.2 g of the title compound. Mp.: 172° C.

$^1$H-NMR (DMSO-$d_6$) 7.85 ppm (m, 1H), 7.0-6.9 (m, 2H), 3.67 (m, 4H), 2.85 (m, 4H).

b.) 2-Amino-5-(morpholin-4-yl)benzoic acid

The mixture of 6 g of 2-nitro-5-(morpholin-4-yl)benzoic acid, 15 mL of cyclohexene and 3 g of Pd/C (10%) is heated under reflux conditions in 120 mL of ethanol for 6 hours. The hot reaction mixture is filtered through celite filter. The filtrate is evaporated to obtain 4.8 g of the title compound. m.p.: 242° C.

$^1$H-NMR (DMSO-$d_6$) 7.25 ppm (m, 1H), 6.96 (m, 1H), 6.62 (m, 1H), 3.69 (m, 4H), 2.85 (m, 4H).

c.) 5-(Morpholin-4-yl)isatoic anhydride

To the mixture of 8.9 g of 2-amino-5-(morpholin-4-yl) benzoic acid in 60 mL of dioxane, under stirring and external cold water cooling 10 mL of diphosgene is added dropwise. The mixture is heated under reflux conditions for 4 hours. From the cold reaction mixture the solid material is filtered off, washed with 50 mL of ether. The product is stirred for 5 minutes in the mixture of 50 mL of methanol and 5 mL of triethylamine, it is filtered off and washed with 30 mL of methanol. After drying 7 g of the title product is obtained, m.p.: 235° C.

$^1$H-NMR (DMSO-$d_6$) 7.8 ppm (m, 1H), 6.78 (m, 1H), 6.66 (m, 1H), 3.73 (m, 4H), 2.92 (m, 4H).

d.) 2-Amino-3-cyano-4-hydroxy-6-(morpholin-4-yl) quinoline 4 g of malonitrile is dissolved in 50 mL of dimethylformamide. To the solution, in several portions, 2.4 g of 60% oily dispersion of sodium hydride are added. To the clear solution 8 g of 5-(morpholin-4-yl)isatoic anhydride is added and the mixture is stirred at room temperature for 10 hours. The reaction mixture is diluted with 70 mL of water and extracted with 2×30 mL of ethyl acetate. The aqueous phase is evaporated in vacuum, the solid residue is dissolved in 20 mL of water, the pH is adjusted to 6 with acetic acid. The precipitated material is filtered off, washed with water. After drying 6.5 g of the title compound is obtained, m.p.: 291° C.

$^1$H-NMR (DMSO-$d_6$) 7.27 ppm (m, 1H), 7.14 (m, 1H), 7.03 (m, 1H), 3.74 (m, 4H), 3.12 (m, 4H).

e.) 2-Amino-3-cyano-4-chloro-6-(morpholin-4-yl) quinoline

The mixture of 1.7 g of 2-amino-3-cyano-4-hydroxy-6-(morpholin-4-yl)quinoline and 3.4 mL of phosphoryl chloride is stirred at 120° C. for 4 hours. The cooled reaction mixture is poured onto 30 g of ice, the pH of the mixture is adjusted to 8 with 10% NaOH solution, and the precipitated material is filtered off. After drying 1.5 g of the title compound is obtained, m.p.: 206° C.

$^1$H-NMR (DMSO-$d_6$) 7.69 ppm (m, 1H), 7.49 (m, 1H), 7.08 (m, 1H), 6.83 (s, 2H), 3.74 (m, 4H), 3.08 (M, 4H).

f.) 2-Amino-3-cyano-4-benzylamino-6-(morpholin-4-yl)quinoline 3 g of 2-amino-3-cyano-4-chloro-6-(morpholin-4-yl) quinoline and 6 mL of benzylamine are stirred at 125° C. for 3 hours. The reaction mixture is poured onto 30 mL of water. The precipitated material is filtered off, washed with 20 mL of water. After drying 2.3 g of the title compound is obtained, m.p.: 202° C.

$^1$H-NMR (DMSO-$d_6$) 8.14 ppm (m, 1H), 7.5-7.2 (m, 8H), 5.85 (s, 2H), 5.04 (d, 2H), 3.65 (m, 4H), 3.1 (m, 4H).

g.) 4-Methoxy-N-(4-methoxybenzoyl)-N-(6-(morpholin-4-yl)-4-benzylamino-3-cyanoquinolin-2-yl) benzamide To the solution of 0.4 g of 2-amino-3-cyano-4-benzylamino-6-(morpholin-4-yl)quinoline in 2 mL of pyridine, 0.4 mL of 4-methoxybenzoyl chloride is added under stirring and cooling. The reaction mixture is stirred at 80° C. for 8 hours, and then poured onto 5 mL of ice-water. The precipitated material is filtered off, washed twice with 3 mL of water. After drying 0.53 g of the title compound is obtained, m.p.: 157° C.

$^1$H-NMR (DMSO-$d_6$) 8.92 ppm (t, 1H), 8.32 (m, 4H), 7.61 (m, 3H), 7.38 (m, 5H), 7.12 (m, 4H), 5.1 (d, 2H), 3.82 (m, 8H).

h.) 4-Methoxy-N-[(6-(morpholin-4-yl)-4-benzylamino-3-cyanoquinolin-2-yl]benzamide To the solution of 2.3 g of 4-methoxy-N-(4-methoxybenzoyl)-N-(6-(morpholin-4-yl)-4-benzylamino-3-cyanoquinolin-2-yl)benzamide in 20 mL of acetonitrile, 5 mL of 1N methanolic potassium hydroxide solution is added. The reaction mixture is heated under reflux conditions for 10 minutes, 1.5 mL of glacial acetic acid is added to it, then it is neutralized with 15 mL of 1M sodium hydrogen carbonate solution. The precipitate is filtered off, the yellow crystalline material is recrystallized from the mixture of 5 mL of dimethylformamide and 40 mL of ethanol. After drying 1.3 g of the title compound is obtained, m.p.: 260° C.

$^1$H-NMR (DMSO-$d_6$) 10.5 ppm (s, 1H), 8.92 (t, 1H), 8.4 (m, 2H), 7.66 (m, 3H), 7.35 (m, 5H), 7.05 (, 2H), 5.1 (d, 2H), 3.82 (m, 8H).

Example 2

4-Methoxy-N-[6-(4-methylpiperazin-1-yl)-4-benzylamino-3-cyanoquinolin-2-yl]benzamide In the general formula (I) $R^1$ and $R^2$ stand for hydrogen atom, $R^3$ for phenyl, group a.) for 4-methylpiperazin-1-yl, $R^6$ for 4-methoxyphenyl, X for NH and the value of N is 1.

a.) 2-Nitro-5-(4-methylpiperazin-1-yl)benzoic acid

The mixture of 10 g of 2-nitro-5-chlorobenzoic acid and 30 mL of N-methylpiperazine is stirred at 120° C. for 6 hours. To the reaction mixture 150 mL of ethyl acetate is added. The precipitated yellow crystalline material is filtered off, dissolved in 15 mL of water. The pH of the mixture is adjusted to 6 with acetic acid. The precipitated material is filtered off, washed with water and dried, to obtain 11.2 g of the title compound. m.p.: 212° C.

$^1$H-NMR (DMSO-$d_6$) 7.89 ppm (d, 1H), 7.03-6.93 (m, 2H), 3.7-3.45 (m, 8H), 2.25 (s, 3H).

b.) 2-Amino-5-(4-methylpiperazin-1-yl)benzoic acid

The mixture of 9 g of 2-nitro-5-(4-methylpiperazino)benzoic acid, 20 mL of cyclohexene and 3.5 g of Pd/C (10%) is heated under reflux conditions in 120 mL of ethanol for 6 hours. The hot reaction mixture is filtered through celite filter. The filtrate is evaporated to obtain 3.5 g of the title compound. m.p.: 212° C.

$^1$H-NMR (DMSO-$d_6$) 7.19 ppm (d, 1H), 7.06 (m, 1H), 6.69 (d, 1H), 2.9 (m, 4H), 2.43 (m, 4H), 2.22 (s, 3H).

c.) 5-(4-methylpiperazin-1-yl)isatoic anhydride

To the mixture of 5.3 g of 2-amino-5-(4-methylpiperazino) benzoic acid in 30 mL of dioxane, under stirring and external cold water cooling 6 mL of diphosgene is added dropwise. The mixture is heated under reflux conditions for 4 hours. From the cold reaction mixture the solid material is filtered off, washed with 50 mL of ether. The product is stirred for 5 minutes in the mixture of 50 mL of methanol and 5 mL of triethylamine, filtered off, washed with 30 mL of methanol. After drying 5.4 g of the title product is obtained, m.p.: 285° C.

$^1$H-NMR (DMSO-$d_6$) 7.81 ppm (m, 1H), 6.73 (m, 1H), 6.62 (m, 1H), 3.73-2.92 (m, 8H), 2.23 (s, 3H).

d.) 2-Amino-3-cyano-4-hydroxy-6-(4-methylpiperazin-1-yl)quinoline 2 g of malonitrile is dissolved in 30 mL of dimethylformamide. To the solution, in several portions, 1.3 g of 60% oily dispersion of sodium hydride are added. To the clear solution 6.5 g of 5-(4-methylpiperazino)isatoic acid anhydride is added and the mixture is stirred at room temperature for 10 hours. The reaction mixture is diluted with 70 mL of water and extracted with 2×30 mL of ethyl acetate. The aqueous phase is evaporated in vacuum, the solid residue is dissolved in 20 mL of water, the pH is adjusted to 6 with acetic acid. The precipitated material is filtered off, washed with water. After drying 5.2 g of the title compound is obtained, m.p.: 156° C.

hu 1H-NMR (DMSO-$d_6$) 7.23 ppm (m, 1H), 7.12 (m, 1H), 7.03 (m, 1H), 3.65-2.83 (m, 8), 2.1 (s, 3H).

e.) 2-Amino-3-cyano-4-chloro-6-(4-methylpiperazin-1-yl)quinoline

The mixture of 2 g of 2-amino-3-cyano-4-hydroxy-6-(4-methylpiperazino)quinoline and 4 mL of phosphoryl chloride is stirred at 120° C. for 4 hours. The cooled reaction mixture is poured onto 40 g of ice, the pH of the mixture is adjusted to 8 with 10% NaOH solution, and the precipitated material is filtered off. After drying 1.5 g of the title compound is obtained, m.p.: 189° C.

$^1$H-NMR (DMSO-$d_6$) 7.69 ppm (m, 1H), 7.49 (m, 1H), 7.08 (m, 1H), 6.83 (s, 2H), 3.25-2.57 (m, 8H), 2.29 (s, 3H).

f.) 2-Amino-3-cyano-4-benzylamino-6-(4-methylpiperazin-1-yl)quinoline 3 g of 2-amino-3-cyano-4-chloro-6-(4-methylpiperazino) quinoline and 6 mL of benzylamine are stirred at 125° C. for 3 hours. The reaction mixture is poured onto 30 mL of water. The precipitated material is filtered off, washed with 20 mL of water. After drying 2.3 g of the title compound is obtained, m.p.: 176° C.

$^1$H-NMR (DMSO-$d_6$) 8.5 ppm (t, 1H), 7.5-7.15 (m, 8H), 5.85 (s, 2H), 5.04 (d, 2H), 3.65-3.12 (m, 8H), 2.23 (s, 3H).

g.) 4-Methoxy-N-(4-methoxybenzoyl)-N-[6-(4-methylpiperazin-1-yl)-4-benzylamino-3-cyanoquinolin-2-yl]benzamide To the solution of 0.6 g of 2-amino-3-cyano-4-benzylamino-6-(4-methylpiperazino)quinoline in 2 mL of pyridine, 0.6 mL of 4-methoxybenzoyl chloride is added under stirring and cooling. The reaction mixture is stirred at 80° C. for 8 hours, and then poured onto 5 mL of ice-water. The precipitated material is filtered off, washed twice with 3 mL of water. After drying 0.63 g of the title compound is obtained, m.p.: 176° C.

$^1$H-NMR (DMSO-$d_6$) 8.39 ppm (m, 1H), 7.95 (m, 2H), 7.47 (m, 5H), 7.32 (m, 5H), 7.14 (m, 4H), 5.1 (m, 2H), 3.82 (s, 3H), 3.52-2.98 (m, 8H), 2.25 (s, 3H).

h.) 4-Methoxy-N-[6-(4-methylpiperazin-1-yl)-4-benzylamino-3-cyanoquinolin-2-yl]benzamide To the solution of 2.3 g of 4-methoxy-N-(4-methoxybenzoyl)-N-(6-(4-methylpiperazino)-4-benzylamino-3-cyanoquinolin-2-yl)benzamide in 15 mL of acetonitrile, 4 mL of 1N methanolic potassium hydroxide solution is added. The reaction mixture is heated under reflux conditions for 10 minutes, 1 mL of glacial acetic acid is added to it, then it is neutralized with 12 mL of 1M sodium hydrogen carbonate solution. The precipitate is filtered off, the yellow crystalline material is recrystallized from the mixture of 15 mL of methanol and 35 mL of water. After drying 1.1 g of the title compound is obtained, m.p.: 173° C.

$^1$H-NMR (DMSO-$d_6$) 10.53 ppm (m, 1H), 8.39 (m, 1H), 7.95 (m, 2H), 7.57 (m, 3H), 7.34 (m, 5H), 7.04 (m, 2H), 5.1 (m, 2H), 3.82 (s, 3H), 3.52-2.98 (m, 8H), 2.25 (s, 3H).

Example 3

4-Methoxy-N-(6-dimethylamino-4-benzylamino-3-cyanoquinolin-2-yl)benzamide

In the general formula (I) $R^1$ and $R^2$ stand for hydrogen atom, $R^3$ for phenyl, $R^4$ and $R^5$ for methyl group, $R^6$ for 4-methoxyphenyl, X for NH and the value of n is 1.

a.) 2-Nitro-5-dimethylaminobenzoic acid

The mixture of 5 g of 2-nitro-5-chlorobenzoic acid and 15 mL of 60% aqueous dimethylamine solution is stirred at 100° C. for 6 hours. The reaction mixture is evaporated, the residue dissolved in 15 mL of water. The pH of the mixture is adjusted to 6 with acetic acid. The precipitated yellow crystalline material is filtered off, washed with water and dried, to obtain 3.4 g of the title compound. Mp.: 189° C.

$^1$H-NMR (DMSO-$d_6$) 7.78 ppm (d, 1H), 6.59 (m, 1H), 6.48 (m, 1H), 3.0 (s, 6H).

b.) 2-Amino-5-dimethylaminobenzoic acid

The mixture of 2.1 g of 2-nitro-5-dimethylaminobenzoic acid, 7 mL of cyclohexene and 1.5 g of Pd/C (10%) is heated under reflux conditions in 60 mL of ethanol for 6 hours. The hot reaction mixture is filtered through celite filter. The filtrate is evaporated to obtain 1.1 g of the title compound. M.p.: 232° C.

$^1$H-NMR (DMSO-$d_6$) 7.01 ppm (m, 1H), 6.84 (m, 1H), 6.78 (m, 1H), 2.88 (s, 6H).

c.) 5-Dimethylaminoisatoic anhydride

To the mixture of 8.9 g of 2-amino-5-dimethylaminobenzoic acid in 60 mL of dioxane, under stirring and external cold water cooling 10 mL of diphosgene is added dropwise. The mixture is heated under reflux conditions for 4 hours. From the cold reaction mixture the solid material is filtered off, washed with 50 mL of ether. The product is stirred for 5 minutes in the mixture of 50 mL of methanol and 5 mL of triethylamine, filtered off, washed with 30 mL of methanol. After drying 7 g of the title product is obtained, m.p.: 258° C.

$^1$H-NMR (DMSO-$d_6$) 7.56 ppm (m, 1H), 7.42 (m, 1H), 7.13 (m, 1H), 2.97 (s, 6H).

d.) 2-Amino-3-cyano-4-hydroxy-6-dimethylaminoquinoline

To the solution of 4 g of malonitrile in 50 mL of dimethylformamide in several portions 2.4 g of sodium hydride 60% oily dispersion is added. To the clear solution 8 g of 5-dimethylamino-isatoic anhydride is added and the mixture is stirred at room temperature for 10 hours. The mixture is diluted with 70 mL of water and extracted with 2×30 mL of ethyl acetate. The aqueous phase is evaporated in vacuum, the solid residue is dissolved in 20 mL of water, the pH is adjusted to 6 with acetic acid. The precipitated material is filtered off, and washed with water. After drying 6.5 g of the title compound is obtained, m.p.: 360° C.

$^1$H-NMR (DMSO-$d_6$) 7.43 ppm(m, 1H), 7.23(m, 1H), 7.11 (m, 1H), 2.95(s, 6H).

e.) 2-Amino-3-cyano-4-chloro-6-dimethylaminoquinoline

The mixture of 1.7 g of 2-amino-3-cyano-4-hydroxy-6-dimethylaminoquinoline and 3.4 mL of phosphoryl chloride is stirred at 120° C. for 4 hours. The cooled reaction mixture is poured onto 30 g of ice, the pH of the mixture is adjusted to 8 with 10% NaOH solution and the precipitated material is filtered off. After drying 1.5 g of the title compound is obtained, m.p.: 285° C.

$^1$H-NMR (DMSO-$d_6$) 7.43 ppm(mm, 1H), 7.21(m, 1H), 7.05(m, 1H), 6.75(s, 2H), 2.99(s, 6H).

f.) 2-Amino-3-cyano-4-benzylamino-6-dimethylaminoquinoline 3 g of 2-amino-3-cyano-4-chloro-6-dimethylaminoquinoline and 6 mL of benzylamine are stirred at 125° C. for 3 hours. The reaction mixture is poured onto 30 mL of water. The precipitated material is filtered off, washed with 20 mL of water. After drying 2.3 g of the title compound is obtained, m.p.: 265° C.

$^1$H-NMR (DMSO-$d_6$) 8.55-8.45 ppm(m, 2H), 7.8(m, 1H), 7.5-7.23(m, 7H), 6.25(s, 2H), 5.08(d, 2H), 2.99(s, 6H).

g.) 4-Methoxy-N-(4-methoxybenzoyl)-N-(6-dimethylamino-4-benzylamino-3-cyanoquinolin-2-yl) benzamide To the solution of 0.4 g of 2-amino-3-cyano-4-benzylamino-6-dimethylaminoquinoline in 2 mL of pyridine, 0.4 mL of 4-methoxybenzoyl chloride is added under stirring and cooling. The reaction mixture is stirred at 80° C. for 8 hours, then poured onto 5 mL of ice-water. The precipitated material is filtered off, washed twice with 3 mL of water. After drying 0.53 g of the title compound is obtained, m.p.: 156° C.

$^1$H-NMR (DMSO-$d_6$) 8.35 ppm(m, 1H), 7.9(m, 2H), 7.47 (m, 5H), 7.3(m, 5H), 7.1(m, 4H), 5.12(m, 2H), 3.82(s, 3H), 3.0(s, 6H).

h.) 4-Methoxy-N-(6-dimethylamino-4-benzylamino-3-cyanoquinolin-2-yl)benzamide

To the solution of 2.3 g of 4-methoxy-N-(4-methoxybenzoyl)-N-(6-dimethylamino-4-benzylamino-3-cyanoquinolin-2-yl)benzamide in 20 mL of acetonitrile, 5 mL of 1N methanolic potassium hydroxide solution is added. The reaction mixture is heated under reflux conditions for 10 minutes, 1.5 mL of glacial acetic acid is added to it, then it is neutralized with 15 mL of 1M sodium hydrogen carbonate solution. The precipitate is filtered off, the yellow crystalline material is recrystallized from the mixture of 5 ml of dimethylformamide and 40 mL of ethanol. After drying 1.3 g of the title compound is obtained, m.p.: 185° C.

$^1$H-NMR (DMSO-$d_6$) 10.5 ppm(m, 1H), 8.35(m, 1H), 7.91 (m, 2H), 7.53(m, 3H), 7.3(m, 5H), 7.02(m, 2H), 5. 1(m, 2H), 3.85(s, 3H), 3.0(s, 6H).

Example 4

4-Methoxy-N-(6-dimethylamino-4-[2-furylmethylamino]-3-cyanoquinolin-2-yl)benzamide In the general formula (I) $R^1$ and $R^2$ stand for hydrogen atom, $R^3$ for 2-furyl group, $R^4$ and $R^5$ for methyl group, $R^6$ for 4-methoxyphenyl, X for NH and the value of n is 1.

a.) 2-Amino-3-cyano-4-[2-furylmethylamino]-6-dimethylaminoquinoline 3 g of 2-amino-3-cyano-4-chloro-6-dimethylaminoquinoline and 6 mL of furfurylamine are stirred at 125° C. for 3 hours. The reaction mixture is poured onto 30 mL of water. The precipitated material is filtered off, washed with 20 mL of water. After drying 2.05 g of the title compound is obtained, m.p.: 235° C.

$^1$H-NMR (DMSO-$d_6$) 8.7 ppm(m, 1H), 7.6(m, 1H), 7.35-7.23(m, 3H), 6.8 (s, 2H), 6.4(m, 2H), 5.06(d, 2H), 2.96(s, 6H).

b.) 4-Methoxy-N-(4-methoxybenzoyl)-N-(6-dimethylamino-4-[2-furylmethylamino]-3-cyanoquinolin-2-yl)benzamide To the solution of 0.4 g of 2-amino-3-cyano-4-[2-furylmethylamino]-6-dimethylaminoquinoline in 2 mL of pyridine, 0.4 mL of 4-methoxybenzoyl chloride is added under stirring and cooling. The reaction mixture is stirred at 80° C. for 8 hours, then poured onto 5 mL of ice-water. The precipitated material is filtered off, washed twice with 3 mL of water. After drying 0.5 g of the title compound is obtained, m.p.: 143° C.

$^1$H-NMR (DMSO-$d_6$) 8.35 ppm(m, 1H), 7.9-7.1(m, 14H), 5.12(m, 2H), 3.82(s, 6H), 3.0(s, 6H).

c.) 4-Methoxy-N-(6-dimethylamino-4-[2-furylmethylamino]-3-cyanoquinolin-2-yl)benzamide To the solution of 2.3 g of 4-methoxy-N-(4-methoxybenzoyl)-N-(6-dimethylamino-4-[2-furylmethylamino]-3-cyanoquinolin-2-yl)benzamide in 20 mL of acetonitrile, 5 mL of 1N methanolic potassium hydroxide solution is added. The reaction mixture is heated under reflux conditions for 10 minutes, 1.5 mL of glacial acetic acid is added to it, then it is neutralized with 15 mL of 1M sodium hydrogen carbonate solution. The precipitate is filtered off, the yellow crystalline material is recrystallized from the mixture of 5 ml of dimethylformamide and 40 mL of ethanol. After drying 1.1 g of the title compound is obtained, m.p.: 195° C.

$^1$H-NMR (DMSO-$d_6$) 10.5 ppm(m, 1H), 8.25(t, 1H), 7.98 (m, 2H), 7.63-7.03(m, 7H), 6.42 (d, 1H), 5.04(d, 2H), 3.85(s, 3H), 3.05(s, 6H).

Example 5

4-Methoxy-N-(6-dimethylamino-4-[2-thienylmethylamino]-3-cyanoquinolin-2-yl)benzamide In the general formula (I) $R^1$ and $R^2$ stand for hydrogen atom, $R^3$ for 2-thienyl group, $R^4$ and $R^5$ for methyl group, $R^6$ for 4-methoxyphenyl,X for NH and the value of n is 1.

a.)-2-Amino-3-cyano-4-[2-thienylmethylamino]-6-dimethylaminoquinoline 3 g of 2-amino-3-cyano-4-chloro-6-dimethylaminoquinoline and 6 mL of 2-thienylmethylamine are stirred at 125° C. for 3 hours. The reaction mixture is poured onto 30 mL of water. The precipitated material is filtered off, washed with 20 mL of water. After drying 1.9 g of the title compound is obtained, m.p.: 211° C.

$^1$H-NMR (DMSO-$d_6$) 8.2 ppm(m, 1H), 7.46-6.95(m, 6H), 6.08(s, 2H), 5.18(d, 2H), 2.94(s, 6H).

b.) 4-Methoxy-N-(4-methoxybenzoyl)-N-(6-dimethylamino-4-[2-thienylmethylamino]-3-cyano-quinolin-2-yl)benzamide To the solution of 0.4 g of 2-amino-3-cyano-4-[2-thienylmethylamino]-6-dimethylaminoquinoline in 2 mL of pyridine, 0.4 mL of 4-methoxybenzoyl chloride is added under stirring and cooling. The reaction mixture is stirred at 80° C. for 8 hours, then poured onto 5 mL of ice-water. The precipitated material is filtered off, washed twice with 3 mL of water. After drying 0.43 g of the title compound is obtained, m.p.: 171° C.

$^1$H-NMR (DMSO-$d_6$) 8.35 ppm(m, 1H), 7.9-7.05(m, 14H), 5.12(m, 2H), 3.82(s, 6H), 3.0(s, 6H).

c.) 4-Methoxy-N-(6-dimethylamino-4-[2-thienylmethylamino]-3-cyanoquinolin-2-yl)benzamide To the solution of 2.3 g of 4-methoxy-N-(4-methoxybenzoyl)-N-(6-dimethylamino-4-[2-thienylmethylamino]-3-cyanoquinolin-2-yl)benzamide in 20 mL of acetonitrile, 5 ML of 1N methanolic potassium hydroxide solution is added. The reaction mixture is heated under reflux conditions for 10 minutes, 1.5 mL of glacial acetic acid is added to it, then it is neutralized with 15 mL of 1M sodium hydrogen carbonate solution. The precipitate is filtered off, the yellow crystalline material is recrystallized from the mixture of 5 ml of dimethylformamide and 40 mL of ethanol. After drying 1.15 g of the title compound is obtained, m.p.: 163° C.

$^1$H-NMR (DMSO-$d_6$) 10.5 ppm(m, 1H), 8.3(t, 1H), 7.98 (m, 2H), 7.63-6.96(m, 8H), 5.2(d, 2H), 3.85(s, 3H), 3.05(s, 6H).

Example 6

4-Methoxy-N-[6-(piperazin-1-yl)-4-benzylamino-3-cyanoquinolin-2-yl]benzamide

In the general formula (I) $R^1$ and $R^2$ stand for hydrogen atom, $R^3$ for phenyl, group a.) for piperazino, $R^6$ for 4-methoxyphenyl, X for NH and the value of n is 1.

a.) 2-Nitro-5-(4-benzylpiperazin-1-yl)benzoic acid

The mixture of 20 g of 2-nitro-5-chlorobenzoic acid and 50 mL of N-benzylpiperazine is stirred at 120° C. for 6 hours. To the reaction mixture 250 mL of ethyl acetate is added. The precipitated yellow crystalline material is filtered off, dissolved in 200 mL of water. The pH of the mixture is adjusted to 6 with acetic acid. The precipitated material is filtered off, washed with water and dried, to obtain 30 g of the title compound. M.p.: 172° C.

$^1$H-NMR (DMSO-$d_6$) 7.8-6.7 ppm (m, 8H), 3.5 (s, 2H), 3.5-2.8 (m, 8H).

b.) 2-Amino-5-(4-benzylpiperazin-1-yl)benzoic acid

The mixture of 6 g of 2-nitro-5-(4-benzylpiperazin-1-yl) benzoic acid, 15 mL of cyclohexene and 3 g of Pd/C (10%) is heated under reflux conditions in 120 mL of ethanol for 6 hours. The hot reaction mixture is filtered through celite filter. The filtrate is evaporated to obtain 4.8 g of the title compound. m.p.: 242° C.

$^1$H-NMR (DMSO-$d_6$) 7.5-6.8 ppm (m, 8H), 3.68 (s, 3H), 3.5-2.95 (m, 8H).

c.) 5-(4-benzylpiperazin-1-yl)isatoic anhydride

To the mixture of 15 g of 2-amino-5-(4-benzylpiperazin-1-yl)benzoic acid in 90 mL of dioxane, under stirring and external cold water cooling 12.7 mL of diphosgene is added dropwise. The mixture is heated under reflux conditions for 4 hours. From the cold reaction mixture the solid material is filtered off, washed with 120 mL of ether. The product is stirred for 5 minutes in the mixture of 100 mL of methanol and 10 mL of triethylamine, it is filtered off and washed with 50 mL of methanol. After drying 17 g of the title product is obtained, m.p.: 235° C.

$^1$H-NMR (DMSO-$d_6$) 7.68-7.1 ppm (m, 8H), 3.6 (s, 2H), 3.5-2.5(m, 8H).

d.) 2-Amino-3-cyano-4-hydroxy-6-(4-benzylpiperazin-1-yl)quinoline 6.1 g of malonitrile is dissolved in 100 mL of dimethylformamide. To the solution, in several portions, 3.6 g of 60% oily dispersion of sodium hydride are added. To the clear solution 18 g of 5-(4-benzylpiperazin-1-yl)isatoic anhydride is added and the mixture is stirred at room temperature for 10 hours. The reaction mixture is diluted with 100 mL of water and extracted with 2×50 mL of ethyl acetate. The aqueous phase is evaporated in vacuum, the solid residue is dissolved in 50 mL of water, the pH is adjusted to 6 with acetic acid and refluxed for 5 hours. After cooling the precipitated material is filtered off, washed with water. After drying 14.3 g of the title compound is obtained, m.p.: 291° C.

$^1$H-NMR (DMSO-$d_6$) 7.7-6.5 ppm (m, 10H), 4.2 (s, 2H), 3.5-2.5 (m, 8H), e.) 2-Amino-3-cyano-4-chloro-6-(4-benzylpiperazin-1-yl)quinoline The mixture of 14 g of 2-amino-3-cyano-4-hydroxy-6-(4-benzylpiperazin-1-yl)quinoline and 28 mL of phosphoryl chloride is stirred at 120° C. for 6 hours. The cooled reaction mixture is poured onto 500 g of ice, the pH of the mixture is adjusted to 8 with 10% NaOH solution, and the precipitated material is filtered off. After drying 14.5 g of the title compound is obtained, m.p.: 206° C.

$^1$H-NMR (DMSO-$d_6$) 7.7-7.14 ppm (m, 8H), 6.9 (s, 2H), 3.7 (s, 2H), 3.5-2.5 (m, 8H).

f.) 2-Amino-3-cyano-4-benzylamino-6-(4-benzylpiperazin-1-yl)quinoline 14 g of 2-amino-3-cyano-4-chloro-6-(4-benzylpiperazin-1-yl)quinoline and 28 mL of benzylamine are stirred at 125° C. for 4 hours. The reaction mixture is poured onto 100 mL of water. The precipitated material is filtered off, washed with 2×50 mL of water. After drying 8 g of the title compound is obtained, m.p.: 202° C.

$^1$H-NMR (DMSO-$d_6$) 8.1 ppm (m, 1H), 7.5-7.2 (m, 13H), 5.8 (s, 2H), 5.0 (d, 2H), 3.54 (s,2H), 3.5-2.5 (m, 8H).

g.) 4-Methoxy-N-(4-methoxybenzoyl)-N-(6-(4-benzylpiperazin-1-yl)-4-benzylamino-3-cyanoquinolin-2-yl)benzamide To the solution of 0.9 g of 2-amino-3-cyano-4-benzylamino-6-(4-benzylpiperazin-1-yl)quinoline in 5 mL of ethylacetate containing 0.3 mL of triethylamine, 0.5 mL of 4-methoxybenzoyl chloride is added under stirring and cooling. The reaction mixture is stirred at 80° C. for 8 hours, then poured onto 10 mL of ice-water. The precipitated material is filtered off, washed twice with 3 mL of water. After drying 0.53 g of the title compound is obtained, m.p.: 157° C.

$^1$H-NMR (DMSO-$d_6$) 8.92 ppm (t, 1H), 8.32 (m, 4H), 7.61 (m, 3H), 7.38 (m, 5H),7.12 (m, 4H), 5.1 (d, 2H), 3.82 (s, 6H), 3.56 (s, 2H), 3.5-2.5 (m, 8H).

h.) 4-Methoxy-N-[(6-(4-benzylpiperazin-1-yl)-4-benzylamino-3-cyanoquinolin-2-yl]benzamide To the solution of 2.0 g of 4-methoxy-N-(4-methoxybenzoyl)-N-(6-(4-benzylpiperazin-1-yl)-4-benzylamino-3-cyanoquinolin-2-yl)benzamide in 20 mL of acetonitrile, 4 mL of 1N methanolic potassium hydroxide solution is added. The reaction mixture is heated under reflux conditions for 10 minutes, 1.5 mL of glacial acetic acid is added to it, then it is neutralized with 15 mL of 1M sodium hydrogen carbonate solution. The precipitate is filtered off, the yellow crystalline material is recrystallized from the mixture of 5 mL of dimethylformamide and 40 mL of ethanol. After drying 1.3 g of the title compound is obtained, m.p.: 260° C.

$^1$H-NMR (DMSO-$d_6$) 10.5 ppm (s, 1H), 8.92 (t, 1H), 7.97-7.01 (m, 17H), 5.1 (d, 2H), 3.82 (s, 3H), 3.56 (s, 2H), 3.5-2.5 (m, 8H).

i.) 4-Methoxy-N-[(6-(piperazin-1-yl)-4-benzylamino-3-cyanoquinolin-2-yl]benzamide 1 g of 4-methoxy-N-[(6-(4-benzylpiperazin-1-yl)-4-benzylamino-3-cyanoquinolin-2-yl]benzamide was dissolved in dimethylformamide and water, containing 0.5 mL of acetic acid and was hydrogenated in the presence of 50 mg of Pd/C (10%) for 4 hours at 45° C. After filtration of the catalyst and evaporation of the solvent the crude product was purified by chromathography to give 0.65 g of the title compound, mp: 145° C.

$^1$H-NMR (DMSO-$d_6$) 10.5 ppm (s, 1H), 8.48 (m, 1H), 7.94 (m, 2H), 7.6-7.35 (m, 2H), 7.33 (s, 5H), 7.24 (m, 1H), 7.02 (m, 2H), 5.08 (d, 2H), 3.83 (s, 3H), 3.22 (m, 4H), 2.86 (m, 4H).

Example 7

N-[6-amino-4-(benzylamino)-3-cyanoquinolin-2-yl]-4-methoxybenzamide

In the general formula (I) $R^1$ and $R^2$ stand for hydrogen atom, $R^3$ for phenyl, $NR^4R^5$ stands for $NH_2$, $R^6$ for 4-methoxyphenyl, X for NH and the value of n is 1.

a,) 5-Nitroisatoic anhydride

To the mixture of 37 g of 2-amino-5-nitrobenzoic acid in 500 mL of dioxane, under stirring 24.5 mL of diphosgene was added dropwise. The mixture was heated under reflux conditions for 6 hours then it was evaporated to dryness. The residue was suspended in 100 mL of diethyl ether and filtered off to give 41.4 g of the title product as HCl salt, m.p.: 256-259° C. LC-MS: $MH^+$ 209; Ret. time: 5 minutes.

$^1$H-NMR (DMSO-$d_6$) 8.54 (d, 1H), 8.46 (dd, 1H), 7.37 (d, 1H) ppm.

b,) 2-Amino-3-cyano-4-hydroxy-6-nitroquinoline

To the solution of 47.25 g of 5-nitroisatoic anhydride in 230 mL of DMF 15 g of malonitrile and 63.3 mL of triethylamine were added and the reaction mixture was stirred at 60° C. for 2 hours. The solvent was evaporated at reduced pressure and the residue was mixed with 570 mL of acetonitrile and 114 mL of concd. HCl and the solution was stirred at room temperature overnight. The precipitate was then filtered off, washed with water and ethanol to give 49.7 g of product, m.p.: >360° C. LC-MS: $MH^+$ 231; Ret. time: 4.78 min.

$^1$H-NMR (DMSO-$d_6$) 8.64 (d, 1H), 8.36 (dd, 1H), 7.6 (s, 2H), 7.55 (d, 1H) ppm.

c,) 2-Amino-3-cyano-4-chloro-6-nitroquinoline

The stirred mixture of 48.5 g of 2-amino-3-cyano-4-hydroxy-6-nitroquinoline and 550 mL of phosphoryl chloride was refluxed for 4 hours. The reaction mixture was concentrated to half of its volume and the residue was poured onto 1500 g of ice. The yellow precipitate was filtered off, washed with water to give 60.5 g of solid. 25 g of this solid was stirred at room temperature in 500 mL of 0.5 N HCl for 6 hours, then the precipitate was filtered off, washed with water to give 18.5 g of product, m.p.: >360° C. LC-MS: $MH^+$ 249; Ret. time: 5.94 min.

$^1$H-NMR (DMSO-$d_6$) 8.73 (d, 1H), 8.48 (dd, 1H), 7.92 (d, 1H) ppm.

d,) 2-Amino-3-cyano-4-benzylamino-6-nitroquinoline

A mixture of 7 g of 2-amino-3-cyano-4-chloro-6-nitroquinoline and 30 mL of benzylamine was stirred at 55° C. for 1.5 hours. The reaction mixture is poured onto 30 mL of water. The precipitated material is filtered off, washed with water to give 7 g of the title compound, m.p.: 280-283° C. LC-MS: $MH^+$ 2320; Ret. time: 5.19 minutes.

$^1$H-NMR (DMSO-$d_6$): 9.28 (d, 1H), 8.90 (t, 1H), 8.24 (dd, 1H), 7.3 (m, 5H), 6.98 (s,2H), 5.04 (d, 2H) ppm.

e,) 4-Methoxy-N-(4-methoxybenzoyl)-N-(4-benzylamino-3-cyano-6-nitroquinolin-2-yl)benzamide A suspension of 3.5 g of 2-amino-3-cyano-4-benzylamino-6-nitroquinoline in 50 mL of dry pyridine was refluxed with 5.6 g of 4-methoxybenzoyl chloride for 3.5 hours. The solvent was evaporated in reduced pressure and the residue was suspended in 30 mL of a saturated solution of $Na_2CO_3$ in water. The suspension was extracted with 3×25 mL of $CH_2Cl_2$. The combined organic extract was evaporated to dryness, the residue was dissolved in diethyl ether and the solution was kept in a refrigerator for a night. The precipitate was filtered off, washed with diethyl ether to give 6.25 g of the title compound, m.p.: 145-148° C. LC-MS: $MH^+$ 588; Ret. time: 7.00 min.

f,) N-[(4-Benzylamino-3-cyano-6-nitroquinolin-2-yl]-4-methoxy-benzamide

A suspension of 6.2 g of N-(4-methoxybenzoyl)-N-(4-benzylamino-3-cyano-6-nitroquinolin-2-yl)-4-methoxybenzamide in 75 mL of acetonitrile was refluxed with 25.2 mL of 1N methanolic potassium hydroxide solution for 6 minutes. 4.4 mL of glacial acetic acid was dropped to the solution while hot, cooled and neutralized with 56.3 mL of 1M aqueous $NaHCO_3$ solution. The precipitate was filtered off, washed with water to give 4.1 g of title compound, m.p.: 264-266° C.

$^1$H-NMR (DMSO-$d_6$) 10.9 (s, 1H), 9.55 (d, 1H), 9.28 (t, 1H), 8.77 (d, 1H), 8.48 (dd, 1H), 8.00 (d, 2H), 7.90 (d, 1H), 7.4 (m, 4H), 7.29 (m, 1H), 7.05 (d, 2H), 5.12 (d, 2H), 3.84 (s, 3H) ppm.

g,) N-[6-amino-4-(benzylamino)-3-cyanoquinolin-2-yl]-4-methoxybenzamide

A mixture of 320 mL of ethanol, 80 mL of water, 200 mL of THF, 7.6 g of Fe-powder, and 1 mL of concd. HCl was refluxed for 10 min. 9 g of N-[(4-benzylamino-3-cyano-6-nitroquinolin-2-yl]-4-methoxy-benzamide was then added and the reaction mixture was intensively refluxed for 2 hours and it was cooled to 35° C. The precipitate was filtered off, washed with a 1:1 mixture of $CH_2Cl_2$ and ethanol. The combined organic solution was filtered on charcoal and evaporated to dryness. The residue was suspended in a mixture of 50 mL of water and 10 mL of ethanol, the solid material was filtered off, washed with water to give 6.65 g of the title compound, mp: 228-230° C. LC-MS: $MH^+$ 424; Ret. time: 5.33 minutes.

$^1$H-NMR (DMSO-$d_6$) 10.44 (s, 1H), 8.0 (s+d, 3H), 7.50 (d, 1H), 7.3-7.1 (m, 7H), 7.03 (d, 2H), 5.55 (s, 2H), 5.04 (d, 2H), 3.83 (s, 3H) ppm.

Example 8

N-{6-amino-4-[(2-thienylmethyl)amino)]-3-cyano-quinolin-2-yl}-4-methoxybenzamide In the general formula (I) $R^1$ and $R^2$ stand for hydrogen atom, $R^3$ for 2-thienyl, $NR^4R^5$ stands for $NH_2$, $R^6$ for 4-methoxyphenyl, X for NH and the value of n is 1.

a,) 2-Amino-3-cyano-4-(2-thienylmethyl)amino-6-nitroquinoline

Applying the same procedure as given under Example 7d with the modification that instead of benzylamine, (2-thienylmethyl)amine was used to give 7.1 g of the title compound, m.p.: 277-280° C. LC-MS: $MH^+$ 326; Ret. time: 5.25 min.

b,) N-(4-Methoxybenzoyl)-N-[3-cyano-6-nitro-4-(2-thienylmethyl)-aminoquinolin-2-yl]-4-methoxybenzamide Started the reaction from 2-amino-3-cyano-4-(2-thienylmethyl)amino-6-nitroquinoline (3.6 g) and using the procedure as given for Example 7e, 6.3 g of the title compound was prepared, m.p.: 174-177° C. LC-MS: $MH^+$ 595; Ret. time: 7.16 min.

c,) N-[3-Cyano-6-nitro-4-(2-thienylmethyl)amino-quinolin-2-yl]-4-methoxybenzamide Started the reaction from N-(4-methoxybenzoyl)-N-[3-cyano-6-nitro 4-(2-thienylmethyl)amino]-quinolin-2-yl)-4-methoxybenzamide (6.2 g) and using the procedure as given for Example 7f, 4.3 g of the title compound was prepared, m.p.: 217-220° C. LC-MS: $MH^+$ 460; Ret. time: 6.57 minutes.

$^1$H-NMR (DMSO-$d_6$): 11.0 (s, 1H), 9.50 (s, 1H), 9.29 (s, 1H), 8.48 (dd, 1H), 8.02 (d, 2H), 7.90 (d, 1H), 7.48 (dd, 1H), 7.21 (d, 1H), 7.0 (m, 3H), 5.27 (s, 2H), 3.85 (s, 3H) ppm d,) N-{6-amino-4-[(2-thienylmethyl)amino]-3-cyanoquinolin-2-yl}-4-methoxybenzamide Started the reaction from N-[4-(2-thienylmethyl)amino-3-cyano-6-nitroquinolin-2-yl]-4-methoxybenzamide (10 g) and using the procedure as given for Example 7g, 9.3 g of the title compound was prepared, mp: 200-203° C. LC-MS: $MH^+$ 430; Ret. time: 5.52 minutes.

$^1$H-NMR (DMSO-$d_6$) 10.48 (s, 1H), 7.98 (s+d, 3H), 7.50 (d, 1H), 7.41 (dd, 1H), 7.21 (s, 1H), 7.16 (dd, 1H), 7.11 (d, 1H), 7.04 (d, 2H), 6.98 (dd, 1H), 5.45 (s, 2H), 5.18 (d, 2H), 3.84 (s, 3H) ppm Example 9

N-{4-(benzylamino)-3-cyano-6-(methylamino) quinolin-2-yl}-4-methoxybenzamide

In the general formula (I) $R^1$ and $R^2$ stand for hydrogen atom, $R^3$ for phenyl, $R^4$ stands for Me, $R^5$ stands for H and $R^6$ for 4-methoxyphenyl, X for NH and the value of n is 1.

A suspension of 1 g of N-{4-(benzylamino)-3-cyano-6-aminoquinolin-2-yl}-4-methoxybenzamide and 0.65 g of paraformaldehyde in a mixture of 48 mL of ethanol and 48 mL of $CH_2Cl_2$ was refluxed with 0.5 mL of 54% $HBF_4$ solution in diethyl ether for 1.5 hours. After addition of 0.3 g of $NaBH_4$ the reflux was continued for 1.5 hours followed by addition of a further amount of 0.3 g of $NaBH_4$ and reflux for 2 hours. After repeated addition of 0.25 mL of 54% $HBF_4$ solution in diethyl ether and 0.3 g of $NaBH_4$ the reflux was continued for additional 1.5 hours. The reaction mixture was filtered while hot, the solid was washed with a 1:1 mixture of $CH_2Cl_2$ and ethanol. The combined organic solution was concentrated and the residue was chromatographed on silica gel with a 50:1 mixture of $CHCl_3$ and ethyl acetate to give the crude product. It was recrystallized from a 2:1 mixture of ethanol and DMF to give 0.6 g of title compound, m.p.: 237-240° C. LC-MS: $MH^+$ 438; Ret. time: 5.76 minutes.

$^1$H-NMR (DMSO-$d_6$) 10.43 (s, 1H), 8.18 (t, 1H), 7.94 (d, 2H), 7.50 (d, 1H), 7.3-7.0 (m, 9H), 6.24 (m, 1H), 5.08 (d, 2H), 3.83 (s, 3H), 2.83 (d, 3H) ppm.

Example 10

N-{3-Cyano-6-(formylamino)-4-[(2-thienylmethyl) amino]quinolin-2-yl]-4-methoxybenzamide In the general formula (I) $R^1$ and $R^2$ stand for hydrogen atom, $R^3$ for 2-thienyl, $R^4$ stands for hydrogen, $R^5$ stands for CHO and $R^6$ for 4-methoxyphenyl, X for NH and the value of n is 1.

A suspension of 0.32 g of N-{6-amino-4-[(2-thienylmethyl)amino]-3-cyanoquinolin-2-yl}-4-methoxybenzamide was kept in 60 mL of methyl formate at 100° C. in a closed apparatus (internal pressure: 10 bar) for 7 hours. After cooling the solvent was evaporated and the residue was recrystallized from $CH_2Cl_2$/MeOH to give 0.22 g of title compound, m.p.: 223-226° C. LC-MS: $MH^+$ 458; Ret. time: 5.71 min.

Example 11

{4-(Benzylamino)-3-cyano-2-[(4-methoxybenzoyl)amino]quinolin-6-yl}sulfamic acid

In the general formula (I) $R^1$ and $R^2$ stand for hydrogen atom, $R^3$ for phenyl, $R^4$ stands for H, $R^5$ stands for $SO_2OH$ and $R^6$ for 4-methoxyphenyl, X for NH and the value of n is 1.

To a solution of 5.2 g of $Na_2S_2O_4$ (purity: 85%) in 160 mL of water and 200 mL of ethanol was added 20 mL of aqueous 1N NaOH solution. The solution was heat up to boiling then 2.27 g of N-[(4-benzylamino-3-cyano-6-nitroquinolin-2-yl]-4-methoxybenzamide was added and refluxing was continued for 2 hours. The reaction mixture let stand at room temperature overnight then it was concentrated to half of its volume. The residue was made alkaline (pH=8) by addition of 1N NaOH solution and was extracted with $CH_2Cl_2$. The aqueous solution was acidified to pH=5 by addition of concd. HCl solution and the precipitate was filtered off. The solid was chromatographed on silica gel eluted first by a mixture of ethyl acetate/methanol/25% ammonia=220/30/2, then 200/80/2 to get 0.5 g of title compound as ammonium salt, m.p.: 220-222° C. LC-MS: $MH^+$ 504; Ret. time: 5.56 min.

$^1$H-NMR (DMSO-$d_6$) 10.48 (s, 1H), 8.21 (s, 1H), 8.09 (t, 1H), 7.95 (d, 2H), 7.70 (s, 1H), 7.62 (d, 1H), 7.56 (d, 1H), 7.3 (m, 4H), 7.25 (m, 1H), 7.03 (d, 2H), 5.05 (d, 2H), 3.83 (s, 3H) ppm Example 12

{4-(Benzylamino)-3-cyano-2-[(4-methoxybenzoyl)amino]quinolin-6-yl}methylsulfamic acid In the general formula (I) $R^1$ and $R^2$ stand for hydrogen atom, $R^3$ for phenyl, $R^4$ stands for Me, $R^5$ stands for $SO_2OH$ and $R^6$ for 4-methoxyphenyl, X for NH and the value of n is 1.

A solution of 110 mg of N-{4-(benzylamino)-3-cyano-6-(methylamino)quinolin-2-yl}-4-methoxy-benzamide in 10 mL of pyridine was stirred at room temperature with 0.2 mL of DBU and 150 mg of pyridinium-$SO_3$ komplex for 2 hours. The reaction mixture was concentrated to dryness, the residue was chromatographed on silica gel using a mixture of ethyl acetate/methanol/25% ammonia =200/80/2 as eluent to give 10 mg of title compound as ammonium salt. LC-MS: $MH^+$ 518; Ret. time: 6.22 minutes.

Example 13

N-{4-(Benzylamino)-3-cyano-6-[formyl(methyl)amino]quinolin-2-yl}-4-methoxybenzamide In the general formula (I) $R^1$ and $R^2$ stand for hydrogen atom, $R^3$ for phenyl, $R^4$ stands for Me, $R^5$ stands for CHO and $R^6$ for 4-methoxyphenyl, X for NH and the value of n is 1.

A suspension of 110 mg of N-{4-(benzylamino)-3-cyano-6-(methylamino)quinolin-2-yl}-4-methoxybenzamide was refluxed in 10 mL of ethyl formate for 24 hours. After cooling the precipitated crystals were filtered off, washed with ethyl formate and ethanol to give 30 mg of title compound, m.p.: 237-240° C. LC-MS: $MH^+$ 465; Ret. time: 6.11 min.

Example 14

4-Methoxy-N-[6-(4-formylpiperazin-1-yl)-4-benzylamino-3-cyanoquinolin-2-yl]benzamide In the general formula (I) $R^1$ and $R^2$ stand for hydrogen atom, $R^3$ for phenyl, group a.) for 4-formylpiperazino, $R^6$ for 4-methoxyphenyl, X for NH and the value of n is 1.

A solution of 120 mg of 4-methoxy-N-[6-(piperazin-1-yl)-4-benzylamino-3-cyanoquinolin-2-yl]benzamide in 5 mL of ethyl formate was refluxed for 2 hours. After cooling the solvent was evaporated and the residue was recrystallysed from methanol to give 65 mg of the title compound. mp: 243° C.

$^1$H-NMR (DMSO-$d_6$) 10.6 ppm (s, 1H), 8.48 (m, 1H), 8.1 (s, 1H), 7.94 (m, 2H), 7.6-7.1 (m, 8H), 7.05 (m, 2H), 5.1 (d, 2H), 3.82 (s, 3H), 3.7-3.2 (m, 8H).

Example 15

4-[2-(Benzoylamino)-4-benzylamino)-3-cyanoquinolin-6-yl]piperazine-1-sulfonic acid In the general formula (I) $R^1$ and $R^2$ stand for hydrogen atom, $R^3$ for phenyl, group a.) for 4-sulfonylpiperazino, $R^6$ for 4-methoxyphenyl, X for NH and the value of n is 1.

A solution of 50 mg of 4-methoxy-N-[6-(piperazin-1-yl)-4-benzylamino-3-cyanoquinolin-2-yl]benzamide in 0.5 mL pyridine and pyridinium-$SO_3$ complex was refluxed for 2 hours and working up according to a procedure published in the literature (G. F. Smith and D. A. Taylor, Tetrahedron, 29, 669, 1973).

LC-MS: $MH^+$ 572; Ret. time: 5.9 min.

Structure and physical characteristics of further compounds of the general formula (I), wherein $R^1$ and $R^2$ stand for hydrogen atom, X stands for —NH— and n represents 1, are shown in Table I TABLE I
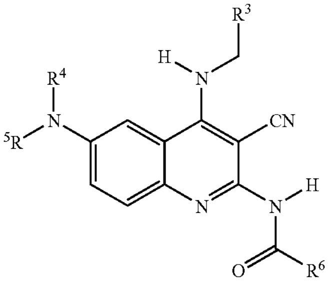
| No | $R^3$ | $R^4$ | $R^5$ | $R^6$ | Mp (° C.) | LC-MS $MH^+$/Ret. time(min) | Process of example |
|---|---|---|---|---|---|---|---|
| 16 | 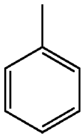 | Me | Me | 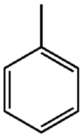 | 211 | | 4 |
| 17 | 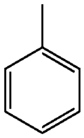 | Me | Me | 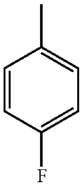 | 208 | | 4 |
| 18 | 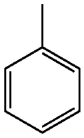 | Me | Me | 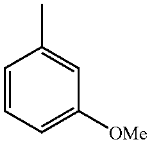 | 198 | | 4 |
| 19 | 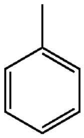 | Me | Me | 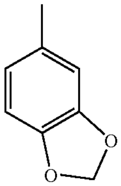 | 176 | | 4 |
| 20 | 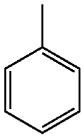 | Me | Me | 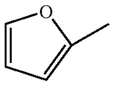 | 152 | | 4 |
| 21 | 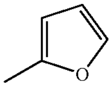 | Me | Me | 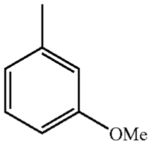 | 163 | | 4 |
| 22 | 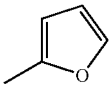 | Me | Me | 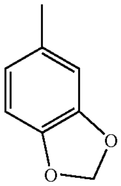 | 172 | | 4 |

TABLE I-continued
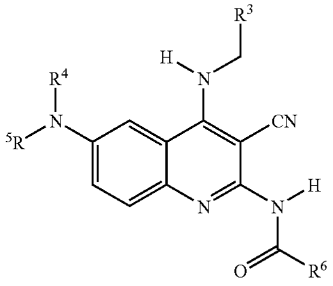
| No | $R^3$ | $R^4$ | $R^5$ | $R^6$ | Mp (° C.) | LC-MS $MH^+$/Ret. time(min) | Process of example |
|---|---|---|---|---|---|---|---|
| 23 | 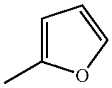 | Me | Me | 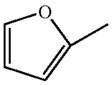 | 158 | | 4 |
| 24 | 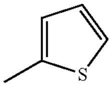 | Me | Me | 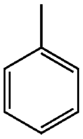 | 170 | | 4 |
| 25 | 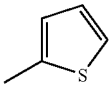 | Me | Me | 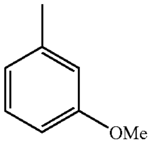 | 171 | | 4 |
| 26 | 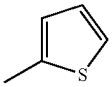 | Me | Me | 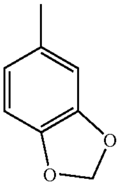 | 165 | | 4 |
| 27 | 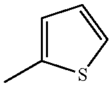 | Me | Me | 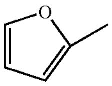 | 148 | | 4 |
| 28 | 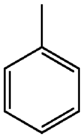 | H | H | 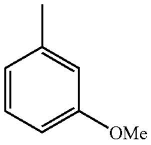 | 235 | 424/5.65 | 7 |
| 29 | 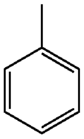 | H | H | 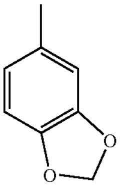 | 234 | 470/6.12 | 7 |
| 30 | 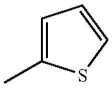 | H | H | 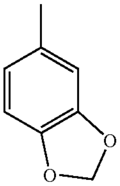 | 222 | 444/5.54 | 7 |

TABLE I-continued
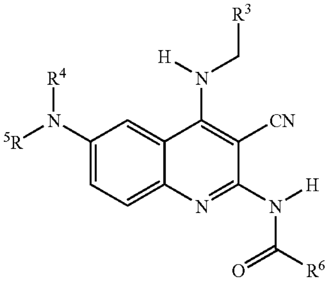
| No | $R^3$ | $R^4$ | $R^5$ | $R^6$ | Mp (° C.) | LC-MS $MH^+$/Ret. time(min) | Process of example |
|---|---|---|---|---|---|---|---|
| 31 | 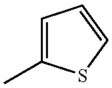 | H | Me | 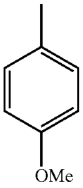 | 160 | 444/5.74 | 9 |
| 32 | 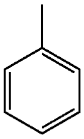 | H | 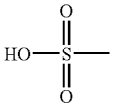 | 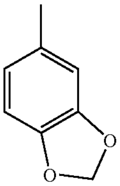 | 217 | 517/5.86 | 11 |
| 33 | 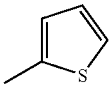 | H | 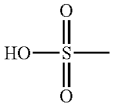 | 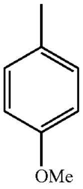 | 257 | 509/5.70 | 11 |
| 34 | 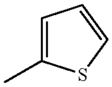 | H | 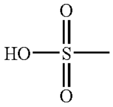 | 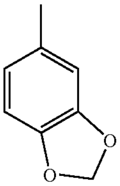 | 208 | 523/5.97 | 11 |
| 35 | 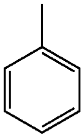 | H | CHO | 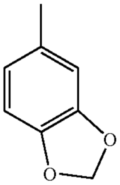 | | 465/7.53 | 10 |
| 36 | 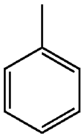 | H | CHO | 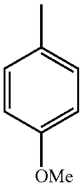 | | 452/5.69 | 10 |

TABLE I-continued

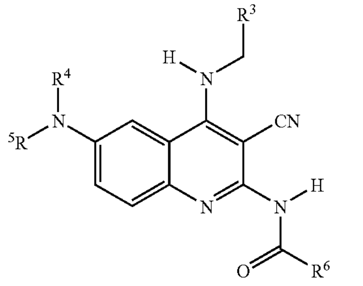

| No | $R^3$ | $R^4$ | $R^5$ | $R^6$ | Mp (° C.) | LC-MS $MH^+$/Ret. time(min) | Process of example |
|---|---|---|---|---|---|---|---|
| 37 | 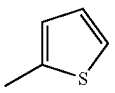 | H | CHO | 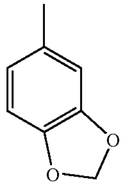 | 247 | 471/5.75 | 10 |
| 38 | 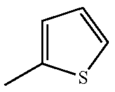 | Me | 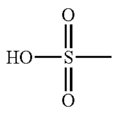 | 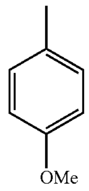 | | 523/6.14 | 12 |
| 39 | 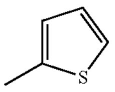 | Me | CHO | 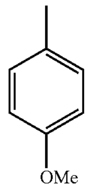 | 248 | 471/5.86 | 13 |

Example 40

Tablets of the following composition are prepared by known methods:

| | |
|---|---|
| Active ingredient: | 25 mg |
| Lactose | 50 mg |
| Avicel | 21 mg |
| Crospovidone | 3 mg |
| Magnesium stearate | 1 mg |

Pharmacological Testing

Biology

Methods

Human adenosine $A_3$ receptor binding

Preparing membrane suspension: ovarium cells of Chinese hamster expressing cloned human $A_3$ receptors (further: CHO-h$A_3$) are appropriately cultured and maintained. Achieving confluent cell layer, the medium is removed from the cells by washing them with 37° C. PBS, then the cell are suspended in ice cold PBS, centrifuged (1000×g 10 min) (Sigma 3K30) and homogenized using teflon homogenizer (B.Braun Potter S) at 1500/min rotation speed, for 15 sec. in the following buffer: 50 mM Tris, 10 mM $MgCl_2$, 1 mM EDTA, pH 8.0. The suspension is centrifuged (43.000 g, 10 min). The pellet is suspended in the above buffer, protein concentration 0.1 mg/ml (Bradford method). Aliquots of the membrane preparation are stored at −80° C.

Binding protocol: incubate CHO-h$A_3$ membrane preparation (2 μg protein content) in incubation buffer (50 mM Tris, 10 mM $MgCl_2$, 1 mM EDTA, 3 U/mL adenosine deaminase, pH 8.0), in the presence of 0.5 nM [$^{125}$I]AB-MECA (p-amino-3-iodo-benzyl-5'-N-methylcarboxamido-adenosine) (100.000 cpm) and 100 μM R-PIA ($N^6$-[L-2-phenylisopropyl]adenosine) to define non-specific binding of test compound in a total volume of 50 μL for 1 hr at room temperature. Filter over Whatman GF/B glass fibre filters (presoaked in 0.5% polyethylenimine for 3 hours), wash 4× with 1 mL ice-cold 50 mM Tris, 10 mM $MgCl_2$, 1 mM EDTA (pH 8.0) on 96-well Brandel Cell Harvester. Detection of activity: in gamma-counter (1470 Wizard, Wallac). Inhibition [%]=100−((activity in the presence of test compound−non-specific activity)/(total activity−non-specific activity))*100

Human Adenosine $A_1$ Receptor Binding

Preparing membrane suspension: ovarium cells of Chinese hamster expressing cloned human $A_1$ receptors (further: CHO-h$A_1$) are appropriately cultured and maintained. Achieving confluent cell layer, the medium is removed from the cells by washing them with 37° C. PBS, then the cell are suspended in ice cold PBS, centrifuged (1000×g 10 min) (Sigma 3K30) and homogenized using teflon homogenizer (B.Braun Potter S) at 1500/min rotation speed, for 15 sec. in the following buffer: 50 mM Tris, 10 mM HCl, pH 7.4. The suspension is centrifuged (43.000 g, 10 min). The pellet is suspended in the above buffer, protein concentration 5 mg/ml (Bradford method). Aliquots of the membrane preparation are stored at −80° C.

Binding protocol: incubate CHO-h$A_1$ membrane preparation (50 μg protein content) in incubation buffer (50 mM Tris, 3 U/mL adenosine deaminase, pH 7.4), 10 nM [$^3$H]CCPA (2-chloro-$N^6$-cyclopenthyl-adenosine) (80,000 dpm) and 10 μM R-PIA ($N^6$-[L-2-phenylisopropyl]adenosine) to define the non-specific binding or test compound in a total volume of 100 μL for 3 hr at room temperature. Filter over Whatman GF/B glass fibre filters (presoaked in 0.5% polyethylenimine for 3 hours), wash 4× with 1 mL ice-cold 50 mM Tris (pH 7.4) on 96-well Brandel Cell Harvester. Detection of activity: in the presence of 200 μL of HiSafe-3 coctail in beta-counter (1450 Microbeta, Wallac). Inhibition [%]=100−((activity in the presence of test compound−non-specific activity)/(total activity−non-specific activity))*100

Human Adenosine $A_{2a}$ Receptor Binding

Binding protocol: Incubate 7 μg of membranes (human $A_{2a}$ adenosine receptors transfected into HEK-293 cells, source: Receptor Biology, Inc.), buffer (50 mM Tris-HCl, 10 mM $MgCl_2$, 1 mM EDTA, 2 U/mL adenosine deaminase, pH 7.4), 20 nM [$^3$H]CGS-21680 (2-[p-(2-carbonylethyl)-phenylethylamino]-5'-N-ethylcarboxamido-adenosine) (200.000 dpm) and 50 μM NECA (5'-N-ethylcarboxamido-adenosine) to define the non-specific binding of test compound, in a total volume of 100 μl for 90 min at room temperature. Filter in vacuum over Whatman GF/B glass fibre filters (presoaked for 3 hours in 0.5% polyethylenimine), wash 4× with 1 mL ice-cold 50 mM Tris, 10 mM $MgCl_2$, 1 mM EDTA, 0.9% NaCl, pH 7.4) on 96-well Brandel Cell Harvester. Detection of activity: in beta-counter (1450 Microbeta, Wallac) in the presence of 200 μL of HiSafe-3 coctail. Inhibition [%]=100−((activity in the presence of test compound−non-specific activity)/(total activity−non-specific activity))*100.

Human adenosine $A_{2b}$ Receptor Binding

Binding protocol: incubate 20.8 μg of membranes (human $A_{2b}$ adenosine receptors transfected into HEK-293 cells, source: Receptor Biology, Inc.), buffer (50 mM Tris-HCl, 10 mM $MgCl_2$, 1 mM EDTA, 0.1 mM benzamidine, 2 U/mL adenosine deaminase, pH 6.5), 32.4 nM [$^3$H]DPCPX (8-cyclopenthyl-1,3-dipropylxanthine) (800.000 dpm) and 100 μM NECA (5'-N-ethylcarboxamido-adenosine) to define non-specific binding or test compound in a total volume of 100 μL for 30 min at room temperature. Filter under 25 mm Hg vacuum over Whatman GF/C glass fibre filters (presoaked in 0.5% polyethylenimine for 3 hours), wash 4× with 1 mL ice-cold 50 mM Tris-HCl (pH 6.5) on 96-well Brandel Cell Harvester. Detection of activity: in the presence of 200 μL of HiSafe-3 coctail in beta-counter (1450 Microbeta, Wallac). Inhibition [%]=100−((activity in the presence of test compound−non-specific activity)/(total activity−non-specific activity))*100

Results

We consider the compounds as biologically active ones if they inhibit the binding of the radioligand on human adenosine $A_3$ receptors with an activity above 80% at 1 μM in our experimental conditions.

The dissociation constant ($K_d$) of [$^{125}$I]AB-MECA on CHO-h$A_3$ membrane preparation is determined by isotope saturation studies with the help of Scatchard analysis (G. Scatchard, Ann. N. Y. Acad. Sci. 51:660, 1949). The $IC_{50}$ is converted to an affinity constant ($K_i$) by application of the Cheng-Prusoff equation (Y. J. Cheng and W. H. Prusoff, Biochem. Pharmacol. 22:3099, 1973).

A number of the compounds of the general formula (I) displayed remarkable biological effects. The most active compounds of the general formula (I) were those defined in claims 2-4. Especially advantageous are the compounds given in the Examples, their $K_i$ values are in the range of 0.5 nM and 900 nM, preferably 0.5 nM and 700 nM. $K_i$ values of the most advantageous compounds are in the range of 0.5 nM 18 nM, most preferably 0.5 and 15 nM.

The compounds possess good bioavailability and a selectivity of at least 3 order of magnitude, in respect to the human adenosine $A_1$, $A_{2a}$ and $A_{2b}$ receptor subtypes.

Further, the duration of their action at intravenous and oral administration is long, their $ED_{50}$ values are low, their toxicological and side-effect profiles are advantageous.

These above data are favourable for the therapeutic application of the compound of the general formula (I).

We claim:

1. A compound of formula (I), (I)

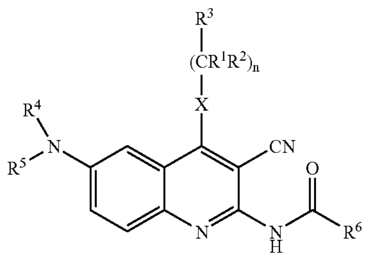

wherein $R^1$ is hydrogen atom or a straight or branched $C_{1-4}$ alkyl;

$R^2$ is hydrogen atom or a straight or branched $C_{1-4}$ alkyl;

$R^3$ is hydrogen atom,
 straight or branched $C_{1-4}$ alkyl, or $C_{3-6}$ cycloalkyl,
 phenyl, thienyl, or furyl, each of which is optionally substituted with one or more straight or branched $C_{1-4}$ alkyl, straight or branched $C_{1-4}$ alkoxy, or halogen atom, or
 six- or five-membered heteroaromatic ring containing one, two or three nitrogen atoms, or five-membered heteroaromatic ring containing one nitrogen atom and one oxygen atom, or one nitrogen atom and one sulphur atom, wherein the heteroaromatic ring is optionally substituted with one or more straight or branched $C_{1-4}$ alkyl, straight or branched $C_{1-4}$ alkoxy, or halogen atom;

$R^4$ and $R^5$ taken together with the nitrogen atom to which they are attached form a group of formula a.)

a.)

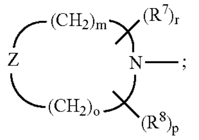

$R^6$ is hydrogen atom, straight or branched $C_{1-4}$ alkyl,
 phenyl, benzyl, thienyl, or furyl, each of which is optionally substituted with methylenedioxy, or one or more straight or branched $C_{1-4}$ alkyl, straight or branched $C_{1-4}$ alkoxy, hydroxy, trifluoromethyl, cyano or halogen atom, or six- or five-membered heteroaromatic ring containing one, two or three nitrogen atoms, or one nitrogen atom and one oxygen atom, or one nitrogen atom and one sulphur atom, wherein the heteroaromatic ring is optionally substituted with one or more straight or branched $C_{1-4}$ alkyl, straight or branched $C_{1-4}$ alkoxy or halogen atom;

$R^7$ and $R^8$ independently are hydrogen atom, straight or branched $C_{1-4}$ alkyl or $C_{3-6}$ cycloalkyl;

X is —$CH_2$—, —NH—, —$NR^9$—, sulphur atom, oxygen atom, sulpho or sulphoxy;

$R^9$ is straight or branched $C_{1-4}$ alkyl or $C_{3-6}$ cycloalkyl;

Z is—O—;

n is zero, 1 or 2;

m is 1, 2, or 3;

o is 1, 2, or 3;

p is zero or 1; and r is zero or 1, or a salt, or tautomer, desmotrop or optically active isomer thereof, or a salt of the tautomer, desmotrop or optically active isomer.

2. The compound according to claim 1, wherein $R^3$ is hydrogen, straight or branched $C_{1-4}$ alkyl, $C_{3-6}$ cycloalkyl, or phenyl, thienyl, or furyl, each of which is optionally substituted with one or more straight or branched $C_{1-4}$ alkyl, straight or branched $C_{1-4}$ alkoxy, or halogen;

a salt or tautomer, desmotrop or optically active isomer thereof, or a salt of the tautomer, desmotrop or optically active isomer.

3. The compound according to claim 1, wherein:

$R^1$ is hydrogen or methyl;

$R^2$ is hydrogen or methyl;

$R^3$ is phenyl, thienyl, or furyl;

$R^6$ stands for 4-methoxyphenyl, 3-methylphenyl, 3-methoxyphenyl, 3,4-methylene-dioxypheny, 4-fluorophenyl, 2-thienyl or 2-furyl;

$R^7$ and $R^8$ independently stand for hydrogen atom, straight or branched $C_{1-4}$ alkyl or $C_{3-6}$ cycloalkyl;

X is —NH—, or —O—;

n is 1;

m is 2;

o is 2;

p is 0; and r is 0, or a salt or tautomer, desmotrop or optically active isomer thereof, or a salt of the tautomer, desmotrop or optically active isomer.

4. The compound according to claim 1, which is:

4-Methoxy-N-[6-(morpholin-4-yl)-4-benzylamino-3-cyanoquinolin-2-yl]-benzamide, or a salt or tautomer, desmotrop or optically active isomer thereof, or a salt of the tautomer, desmotrop or optically active isomer.

5. A process for preparing the compound according to claim 1, comprising selectively hydrolyzing a bis-carboxamide of formula (II"), (II'')

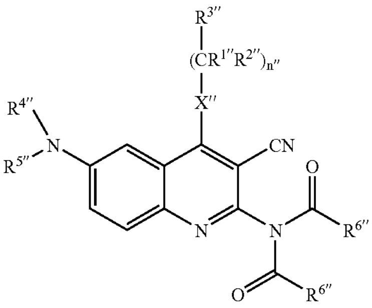

wherein $R^{1''}$ is hydrogen atom or a straight or branched $C_{1-4}$ alkyl;

$R^{2''}$ is hydrogen atom or a straight or branched $C_{1-4}$ alkyl;

$R^{3''}$ is hydrogen atom, straight or branched $C_{1-4}$ alkyl, $C_{3-6}$ cycloalkyl, phenyl, thienyl, or furyl, each of which is optionally substituted by one or more straight or branched $C_{1-4}$ alkyl, straight or branched $C_{14}$ alkoxy, or halogen atom, or six- or five-membered heteroaromatic ring containing one, two or three nitrogen atoms, or five-membered heteroaromatic ring containing one nitrogen atom and one oxygen atom, or one nitrogen atom and one sulphur atom, wherein the heteroaromatic ring is optionally substituted by one or more straight or branched $C_{1-4}$ alkyl, straight or branched $C_{1-4}$ alkoxy, or halogen atom;

$R^{4''}$ and $R^{5''}$ taken together with the nitrogen atom to which they are attached form a nitro or a group of formula a".), a''.)

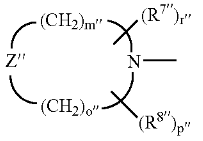

$R^{6''}$ is hydrogen atom or straight or branched $C_{1-4}$ alkyl, phenyl, benzyl, thienyl, or furyl, each of which is optionally substituted with methylenedioxy, or with one or more straight or branched $C_{1-4}$ alkyl, straight or branched $C_{1-4}$ alkoxy, hydroxy, trifluoromethyl, cyano or halogen atom, or six- or five-membered heteroaromatic ring containing one, two or three nitrogen atoms, or one nitrogen atom and one oxygen atom, or one nitrogen atom and one sulphur atom, wherein the heteroaromatic ring is optionally substituted with one or more straight or branched $C_{1-4}$ alkyl, straight or branched $C_{1-4}$ alkoxy or halogen atom;

$R^{7''}$ and $R^{8''}$ independently are hydrogen atom, straight or branched $C_{1-4}$ alkyl or $C_{3-6}$ cycloalkyl;

X" is —$CH_2$—, —NH—, —$NR^{9''}$, sulphur atom, oxygen atom, sulpho or sulphoxy;

$R^{9''}$ is straight or branched $C_{1-4}$ alkyl or $C_{3-6}$ cycloalkyl;

Z" is —O—;

n" is zero, 1 or 2;

m" is 1, 2, or 3;

o" is 1, 2, or 3;

p" is zero or 1; and r" is zero or 1, and optionally removing a protective group.

6. The process according to claim 5, wherein the selective hydrolysis is carried out using alkali hydroxide dissolved in alcoholic medium.

7. A pharmaceutical composition comprising a pharmaceutically effective amount of one or more compounds according to claim 1, or a salt or tautomer, desmotrop or optically active isomer thereof, or a salt of the tautomer, desmotrop or optically active isomer, and one or more auxiliary materials.

8. A pharmaceutical composition comprising a pharmaceutically effective amount of one or more compounds according to claim 3, or a salt or tautomer, desmotrop or optically active isomer thereof, or a salt of the tautomer, desmotrop or optically active isomer, and one or more auxiliary materials.

* * * * *